(12) United States Patent
Davis et al.

(10) Patent No.: US 7,938,826 B2
(45) Date of Patent: May 10, 2011

(54) METHODS, SYSTEMS, AND DEVICES FOR CLOSING A PATENT FORAMEN OVALE USING MECHANICAL STRUCTURES

(75) Inventors: Clark C. Davis, Hollady, UT (US); Scott D. Miles, Sandy, UT (US); Daryl R. Edmiston, Draper, UT (US); Brian K. Whisenant, Salt Lake City, UT (US); Richard J. Linder, Sandy, UT (US); Dewayne C. Fox, South Jordan, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 0 days.

(21) Appl. No.: 11/754,936

(22) Filed: May 29, 2007

(65) Prior Publication Data

US 2008/0033421 A1   Feb. 7, 2008

Related U.S. Application Data

(60) Provisional application No. 60/803,479, filed on May 30, 2006, provisional application No. 60/809,566, filed on May 31, 2006.

(51) Int. Cl.
*A61B 18/14* (2006.01)
(52) U.S. Cl. .............................. 606/41; 606/48; 607/101
(58) Field of Classification Search ................... 606/41, 606/48–50; 607/101, 102, 116
See application file for complete search history.

(56) References Cited

U.S. PATENT DOCUMENTS

| | | | |
|---|---|---|---|
| 4,957,656 A | 9/1990 | Cerny et al. | |
| 5,545,200 A | 8/1996 | West et al. | |
| 5,827,276 A * | 10/1998 | LeVeen et al. | 606/41 |
| 6,022,347 A | 2/2000 | Lindenmeier et al. | |
| 6,050,992 A | 4/2000 | Nichols | |
| 6,063,082 A | 5/2000 | DeVore et al. | |
| 6,197,022 B1 * | 3/2001 | Baker | 606/33 |

(Continued)

FOREIGN PATENT DOCUMENTS

WO    WO/99/18871    4/1999

OTHER PUBLICATIONS

International Search Report dated Jul. 21, 2008, for International Application No. PCT/US07/69995 (2 pages).

(Continued)

*Primary Examiner* — Michael Peffley
(74) *Attorney, Agent, or Firm* — Holland & Hart, LLP

(57) ABSTRACT

A medical device is disclosed that can include a first atrial anchor, a first delivery shaft linked to the first atrial anchor, wherein the first delivery shaft is adapted to move the first atrial anchor, a second atrial anchor, a second delivery shaft linked to the second atrial anchor, wherein the second delivery shaft is adapted to move the second atrial anchor, and a biasing member linking either (i) the first atrial anchor to the first delivery shaft or (ii) the second atrial anchor to the second delivery shaft. The medical device can include an insulation material coupled to one or more of the first or second atrial anchors, or the first or second delivery shaft. A method for treating an internal tissue opening is also disclosed wherein a first and second electrode can be operated between unipolar and bipolar modes to initiate tissue damage, thereby inducing tissue regrowth.

13 Claims, 20 Drawing Sheets

U.S. PATENT DOCUMENTS

| | | | |
|---|---|---|---|
| 6,258,087 B1 * | 7/2001 | Edwards et al. | 606/41 |
| 6,312,429 B1 * | 11/2001 | Burbank et al. | 606/47 |
| 6,325,797 B1 * | 12/2001 | Stewart et al. | 606/41 |
| 6,463,332 B1 | 10/2002 | Aldrich | |
| 6,645,198 B1 | 11/2003 | Bommannan et al. | |
| 6,805,129 B1 | 10/2004 | Pless et al. | |
| 6,908,464 B2 | 6/2005 | Jenkins et al. | |
| 6,939,348 B2 | 9/2005 | Malecki et al. | |
| 6,944,490 B1 | 9/2005 | Chow | |
| 6,970,742 B2 | 11/2005 | Mann et al. | |
| 7,165,552 B2 | 1/2007 | Deem et al. | |
| 7,186,251 B2 * | 3/2007 | Malecki et al. | 606/41 |
| 7,257,450 B2 | 8/2007 | Auth et al. | |
| 7,293,562 B2 | 11/2007 | Malecki et al. | |
| 7,367,975 B2 | 5/2008 | Malecki et al. | |
| 2002/0022864 A1 * | 2/2002 | Mahvi et al. | 607/2 |
| 2004/0158239 A1 * | 8/2004 | Behl et al. | 606/41 |
| 2004/0193147 A1 | 9/2004 | Malecki et al. | |
| 2004/0230185 A1 | 11/2004 | Malecki et al. | |
| 2004/0243122 A1 | 12/2004 | Auth et al. | |
| 2004/0260278 A1 | 12/2004 | Anderson et al. | |
| 2004/0267191 A1 | 12/2004 | Gifford, III et al. | |
| 2005/0021016 A1 | 1/2005 | Malecki et al. | |
| 2005/0033288 A1 | 2/2005 | Auth et al. | |
| 2005/0034735 A1 | 2/2005 | Deem et al. | |
| 2005/0080406 A1 | 4/2005 | Malecki et al. | |
| 2005/0119647 A1 | 6/2005 | He et al. | |
| 2005/0131401 A1 | 6/2005 | Malecki et al. | |
| 2005/0131460 A1 | 6/2005 | Gifford et al. | |
| 2005/0192627 A1 | 9/2005 | Whisenant et al. | |
| 2005/0192654 A1 | 9/2005 | Chanduszko et al. | |
| 2006/0027241 A1 | 2/2006 | Malecki et al. | |
| 2006/0074410 A1 | 4/2006 | Malecki et al. | |
| 2006/0079870 A1 | 4/2006 | Barry | |
| 2006/0241581 A1 | 10/2006 | Malecki et al. | |
| 2006/0241582 A1 | 10/2006 | Malecki et al. | |
| 2006/0241583 A1 | 10/2006 | Malecki et al. | |
| 2006/0241584 A1 | 10/2006 | Malecki et al. | |
| 2006/0247612 A1 | 11/2006 | Malecki et al. | |
| 2006/0271030 A1 | 11/2006 | Francis et al. | |
| 2006/0271040 A1 | 11/2006 | Horne et al. | |
| 2006/0271089 A1 | 11/2006 | Alejandro et al. | |
| 2006/0276779 A1 | 12/2006 | Malecki et al. | |
| 2006/0276846 A1 | 12/2006 | Malecki et al. | |
| 2007/0010806 A1 | 1/2007 | Malecki et al. | |
| 2007/0044811 A1 | 3/2007 | Deem et al. | |
| 2007/0078485 A1 | 4/2007 | Deem et al. | |
| 2007/0088355 A9 | 4/2007 | Auth et al. | |
| 2007/0093804 A1 | 4/2007 | Kaveckis et al. | |
| 2007/0093805 A1 | 4/2007 | Auth et al. | |
| 2007/0100324 A1 | 5/2007 | Tempel et al. | |
| 2007/0106214 A1 | 5/2007 | Gray et al. | |
| 2007/0112347 A1 | 5/2007 | Malecki et al. | |
| 2007/0123824 A1 | 5/2007 | Kaveckis | |
| 2007/0123851 A1 | 5/2007 | Alejandro et al. | |
| 2007/0123852 A1 | 5/2007 | Deem et al. | |
| 2007/0203479 A1 | 8/2007 | Auth et al. | |
| 2007/0287999 A1 | 12/2007 | Malecki et al. | |
| 2008/0009859 A1 | 1/2008 | Auth et al. | |
| 2008/0033425 A1 | 2/2008 | Davis et al. | |

OTHER PUBLICATIONS

International Search Report dated Oct. 25, 2007, for International Application No. PCT/US07/61713 (2 pages).

International Search Report dated Jul. 24, 2008, for International Application No. PCT/US07/69994 (3 pages).

International Search Report dated Jul. 25, 2007, for International Application No. PCT/US06/37691 (2 pages).

* cited by examiner

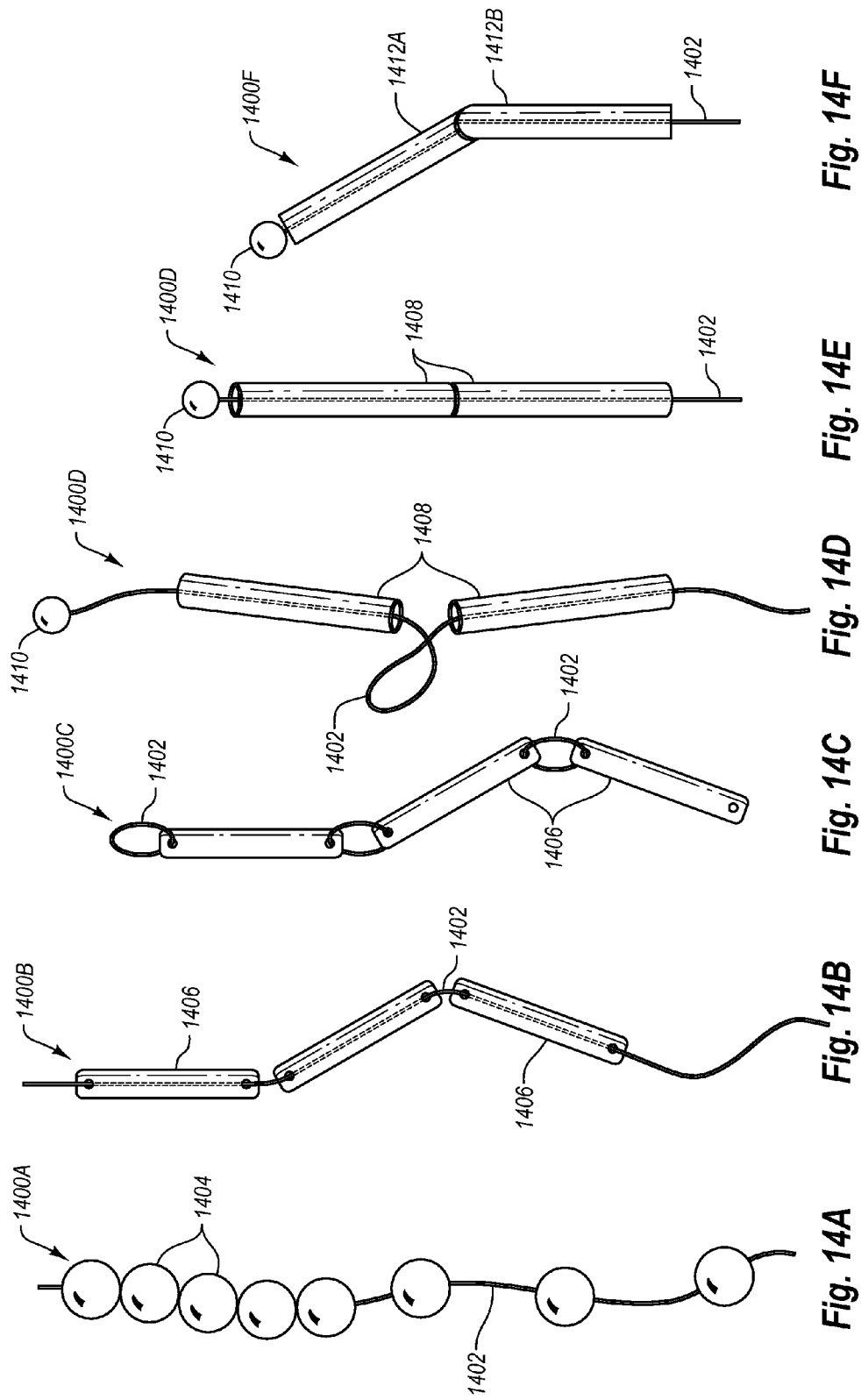

METHODS, SYSTEMS, AND DEVICES FOR CLOSING A PATENT FORAMEN OVALE USING MECHANICAL STRUCTURES

CROSS-REFERENCE TO RELATED APPLICATIONS

This application claims the benefit of U.S. Provisional Application No. 60/803,479, filed May 30, 2006, and U.S. Provisional Application No. 60/809,566, filed May 31, 2006, the contents of each are hereby incorporated by reference in their entirety.

BACKGROUND

1. The Field of the Invention

The present invention relates generally to medical devices and methods of use for closing tissue openings. More particularly, the present invention relates to devices, systems, and methods for closing a patent foramen ovale ("PFO").

2. The Relevant Technology

Physical malformations or defects that are present at birth can be detrimental and even lethal when left uncorrected. A PFO is an example of a cardiac birth defect that can be problematic and even result in death when combined with other factors such as blood clots or other congenital heart defects. A PFO occurs when an opening between the upper two chambers of the heart fail to close during or after birth. This birth defect is sometimes also known as a "hole in the heart."

Some of the problems associated with a PFO can occur when a blood clot travels between the left and right atria of the heart through the PFO, and ends up on the arterial side. A blood clot in the left atrium can be passed through the aorta and travel to the brain or other organs, and cause embolization, stroke, or a heart attack. A PFO can be treated by being closed by a surgical procedure. Additionally, other similar defects (e.g., septal or otherwise) where some tissue needs to be closed in order to function properly can include the general categories of atrial-septal defects ("ASDs"), ventricular-septal defects ("VSCs") and patent ductus arterosus ("PDA"), and the like.

FIGS. 1A-1C depict various views of a heart having a PFO. The heart 10 is shown in a cross-section view in FIG. 1A. In a normal heart 10, the right atrium 30 receives systemic venous blood from the superior vena cava 15 and the inferior vena cava 25, and then delivers the blood via the tricuspid valve 35 to the right ventricle 60. However, in the depicted heart 10 a septal defect, which is shown as a PFO 50, is present between right atrium 30 and left atrium 40.

The PFO 50 is depicted as an open flap on the septum between the heart's right atrium 30 and left atrium 40. In a normal heart 10, the left atrium 40 receives oxygenated blood from the lungs 40 via pulmonary artery 75, and then delivers the blood to the left ventricle 80 via the bicuspid valve 45. In a heart 10 having a PFO 50 some systemic venous blood also passes from the right atrium 30 through the PFO 50 and mixes with the oxygenated blood in left atrium 40, and then is routed to the body from left ventricle 80 via aorta 85.

During fetal development of the heart 10, the interventricular septum 70 divides the right ventricle 60 and left ventricle 80. In contrast, the atrium is only partially partitioned into right and left chambers during normal fetal development, which results in a foramen ovale fluidly coupling the right and left atrial chambers. As shown in FIG. 1B, when the septum primum 52 incompletely fuses with the septum secundum 54 of the atrial wall, the result can be a tunnel 58 depicted as a PFO 50, or an ASD (not shown).

FIG. 1C provides a view of the crescent-shaped, overhanging configuration of the septum secundum 54 from within the right atrium 30 in a heart 10 having a PFO 50. The septum secundum 54 is defined by its inferior aspect 55, corresponding with the solid line in FIG. 1C, and its superior aspect 53 represented by the phantom line, which is its attachment location to the septum primum 52. The septum secundum 54 and septum primum 52 blend together at the ends of the septum secundum 54. The anterior end 56a and posterior end 56p are referred to herein as "merger points" for the septum secundum 54 and septum primum 52. The length of the overhang of the septum secundum 54, which is the distance between superior aspect 53 and inferior aspect 55, increases towards the center portion of the septum secundum as shown.

The tunnel 58 between the right atrium 30 and left atrium 40 is defined by portions of the septum primum 52 and septum secundum 54 between the merger points 56a and 56p which have failed to fuse. The tunnel 58 is often at the apex of the septum secundum 54 as shown. When viewed within right atrium 30, the portion of the septum secundum 54 to the left of tunnel 58, which is referred to herein as the posterior portion 57p of the septum secundum, is longer than the portion of the septum secundum 54 to the right of tunnel 58, which is referred to herein as the anterior portion 57a of the septum secundum. In addition to being typically longer, the posterior portion 57a also typically has a more gradual taper than the anterior portion 57a as shown. The anterior pocket 59a is the area defined by the overhang of the anterior portion 57a of the septum secundum 54 and the septum primum 52, and it extends from the anterior merger point 56a toward the tunnel 58. Similarly, the posterior pocket 59p is the area defined by the overhang of the posterior portion 57p of septum secundum 54 and the septum primum 52, and it extends from the posterior merger point 56p toward the tunnel 58.

Conventional treatments for PFO, and other related conditions have generally involved invasive surgery, which also presents risks to a patient. Although there are some less invasive treatments for PFO, such treatments have been less efficient at closing the PFO opening than techniques involving invasive surgery.

BRIEF SUMMARY OF THE INVENTION

The invention relates to a medical device, system and method of use for reducing the size of an internal tissue opening, such as a Patent Foramen Ovale ("PFO"). In one embodiment, the medical device can include a biasing member, such as a spring. The biasing member can link two spaced apart atrial anchor or can link an atrial anchor or electrode to a delivery shaft for use in positioning the atrial anchor in a heart. The biasing member may alternatively be linked to the right atrial anchor and associated delivery shaft, or may be linked to the left atrial anchor and the left atrial anchor delivery shaft. In this manner, the biasing member can facilitate regulation of the amount of force applied to the PFO during placement of the medical device. In an alternative embodiment, the medical device can include multiple biasing members. For example, in one embodiment, a first spring links the right atrial anchor to a right atrial anchor delivery shaft, and a second spring links the left atrial anchor to a left atrial anchor delivery shaft.

In an alternative embodiment of the invention, the medical device can include insulating layers thereby enabling energy, such as radio frequency ("RF") energy, to be applied to desired tissue areas for treatment of a PFO. For example, insulating layers can be applied to the left atrial anchor, right atrial anchor, a shaft portion which may be positioned in the tunnel of the PFO when the medical device is positioned to treat the PFO, or any combination thereof. The left atrial anchor, right atrial anchor and/or shaft can be conductive to RF energy or can otherwise aid with delivering RF energy to the area of treatment. The insulating layers can be sized and configured so as to enable various amounts of RF energy to pass to adjacently positioned tissue. For example, if a lesser amount of RF energy is to be applied to a desired tissue area, an insulating layer can be used. More insulation can reduce the conductivity of the insulated portion of the medical device.

The invention also relates to a system for treating a PFO by alternating right and left atrial anchors between unipolar and bi-polar modes. Furthermore, the time duration of each application of RF energy can be varied according to determined treatment plans. For example, RF energy can be applied to the PFO by alternating the right and left atrial anchors between unipolar and bi-polar modes, for differing durations. Furthermore, the application of RF energy can be random or repetitive.

In accordance with one embodiment of the invention, the medical device can include first and second atrial anchors each having one or more compliant arms. The compliant arms can be sized and configured to deflect during engagement with tissue surrounding the PFO. In an alternative embodiment, the medical device can include a first atrial anchor, a delivery shaft linked to the first atrial anchor, and one or more hinges linking the first atrial anchor to the delivery shaft, wherein the first atrial anchor can move relative to the delivery shaft.

In an alternative embodiment, the medical device can include a first electrode coupled to the right atrial anchor, and a second electrode coupled to the left atrial anchor. In another embodiment of the invention, the medical device can include a left atrial anchor, a right atrial anchor, and a first and second electrode coupled to either the right or left atrial anchor. In yet another embodiment of the invention, the medical device can also include a right and left atrial anchor which are electrically common elements.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 14A-F illustrate schematic representations of embodiments of a medial device of the present invention;

DETAILED DESCRIPTION

Figure 1A:
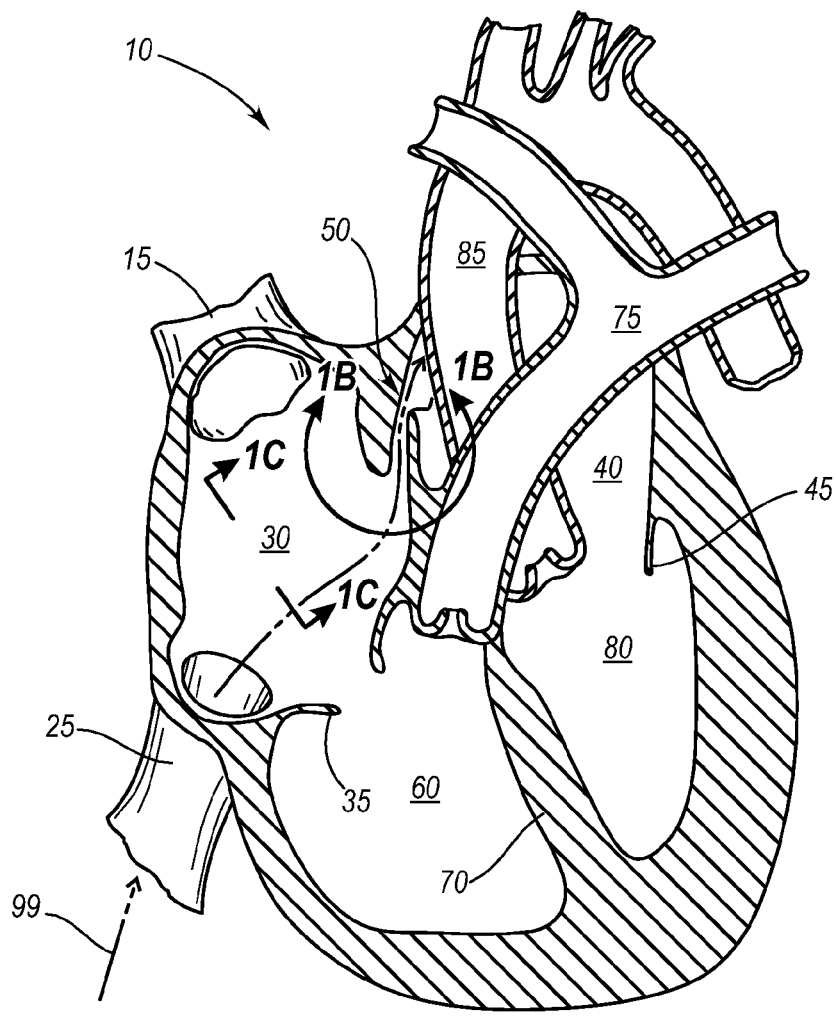
FIG. 1A-1C illustrates exemplary view of a heart having a Patent Foramen Ovale.

The present invention extends to systems, methods, and apparatus for reducing the size of an internal tissue opening. By way of explanation, the devices disclosed herein can be used for a variety of internal tissue opening, although, for purposes of simplicity, frequent reference is made herein to reducing the size of or closing an opening in heart tissue known as Patent Foramen Ovale ("PFO"). Accordingly, it will be understood that references to PFO openings are not limiting of the invention.

In the following description, numerous specific details are set forth to assist in providing an understanding of the present invention. In other instances, aspects of PFO closure devices or medical devices in general have not been described in particular detail in order to avoid unnecessarily obscuring the present invention. In addition, it is understood that the drawings are diagrammatic and schematic representations of certain embodiments of the invention, and are not limiting of the present invention, nor are they necessarily drawn to scale.

Illustrative embodiments of the invention relate to delivering radio frequency or RF energy to tissue adjacent or near to a PFO, such as the septal wall of the heart, to treat the PFO. In order to treat this type of defect it can be desirable to have an electrode system that can position the walls of the flap-like defect toward each other or together while energy is applied to the wall tissue to "weld" the defect closed, i.e. damage the tissue to stimulate tissue growth in the area. Furthermore, it can be desirable to have a system that can enable a practitioner to more effectively determine the morphology of the PFO, the amount of RF energy to apply, as well as the amount of time to apply such amount of RF energy.

In one embodiment, the medical device can include an electrode configured to increase the effectiveness of the tissue weld. The effectiveness of the tissue weld can be increased by configuring the electrode to contact, and in some instances conform with, the tissue of the atrium proximate the opening of the PFO. Furthermore, the electrode can be configured to be collapsible to a small cross section to remove the electrode from the welded tissue opening without substantially interfering with the damaged tissue. While the term electrode is used frequently herein, it will be appreciated that the word anchor can also be used interchangeably with electrode when the electrode also functions to physically pinch or close the PFO, or otherwise physically reduce the size of the PFO. Furthermore, an anchor can also serve as an electrode as needed or can be non-conductive to RF energy or other type of energy usable to "tissue weld" the PFO closed, thus acting as an insulator. Alternatively, the anchor can be partially conductive to RF energy and partially insulated.

The present invention generally includes a medical device, with associated systems and methods, which can be positioned in close proximity to a PFO, used to position the septum secundum and/or septum primum to close the PFO, and then close the PFO using one or more various techniques or methods. The medical device can be positioned either directly or through the use of other medical devices, such as, but not limited to, one or more actuators, catheters, introducer tubes, guidewire, or other medical device(s) that can be used to position and/or actuate the medical device.

The following discussion will be directed to various configurations of the medical devices, systems, and methods according to the present invention, but it will be understood that the described medical devices, systems and methods are only illustrative embodiments and do not limit the applicability of the general disclosure of the invention to other configurations and embodiments of medical devices, systems and methods that are capable of closing an opening within the heart or other body lumen of a patient. Further, although not illustrated, it will be understood that any of the described medical devices, systems, and methods can include an integral soft tip, such as an atraumatic tip, J-hook, etc. to aid with guiding the medical device. In addition, any of the described medical devices, systems, and methods can cooperate with a separate guidewire that aids with navigating and positioning the medical device into the appropriate location, if desirable.

It will be understood by one of ordinary skill in the art in view of the disclosure provided herein that when RF energy is discussed below as a closure means, other methods or means of heating tissue to close a PFO may be utilized, such as optical, laser, acoustic, ultrasonic, hot fluid, resistive, microwave, or other means of heating the tissues. Furthermore, while reference is made specifically to PFO'S, it will be understood that the systems, methods and apparatus of the present invention may be used to reduce the size or close other tissue openings, such as an Atrial Septal Defect (ASD) or other openings in cardiac or other tissues. "Closing" can also refer to joining of tissues, i.e. not necessarily closing an opening, but simply joining tissue to other tissue. Examples include tubal ligation, vascular ligation, wound or defect closure, and others. Also the terms for "electrodes", "anchors", or "clamps" can be generally used interchangeably.

In tissue welding by thermal means, it can be desirable to control the distribution of energy, and thus, heating of the tissue being treated. In the application of RF energy, the energy delivered to the tissues follows an infinite number of parallel paths from one electrode to another or to a ground. The electrical energy will concentrate itself in shorter or lower impedance paths. The following discussion relates to various configurations of medical devices and the energy flow characteristics thereof. The descriptions are primarily for two bipolar electrodes where the current flow is between the two electrodes. However, the principles also hold for unipolar electrodes in which the current flow is between the electrode and a return electrode or ground, which return electrode or ground can be generally placed on the skin of a patient, such as on the patient's leg.

It can be desirable to heat the tissue of the inner surface of the PFO tunnel. However, efficient heating may be obtained when the surrounding tissues are also heated so as to reduce heat migration away from the immediate vicinity of the PFO tunnel to the surrounding tissues. Such heat transfer can reduce the effectiveness of the heat treatment due to certain areas of the tunnel not achieving a desired temperature. Additionally, it can be desirable to heat the tissues surrounding the PFO to create a more generalized response beyond the PFO tunnel. As an example, if tissues surrounding a PFO are damaged, thus promoting a healing response, this may serve to encourage and facilitate the healing response inside the PFO tunnel itself, thus increasing the likelihood of successful PFO closure.

Note also that at RF frequencies, electrical energy may be coupled from electrodes to tissues via either conductive or capacitive means, i.e. even insulated electrodes can be used to heat tissue. The energy transfer characteristics may be modified (but not necessarily eliminated) by insulation thickness, location, or by its presence or absence. In this manner, heating may be accomplished by strategically placing insulation in prescribed amounts along the length of, or on the surfaces of, an electrode to achieve desirable heating patterns.

Figure 2A:
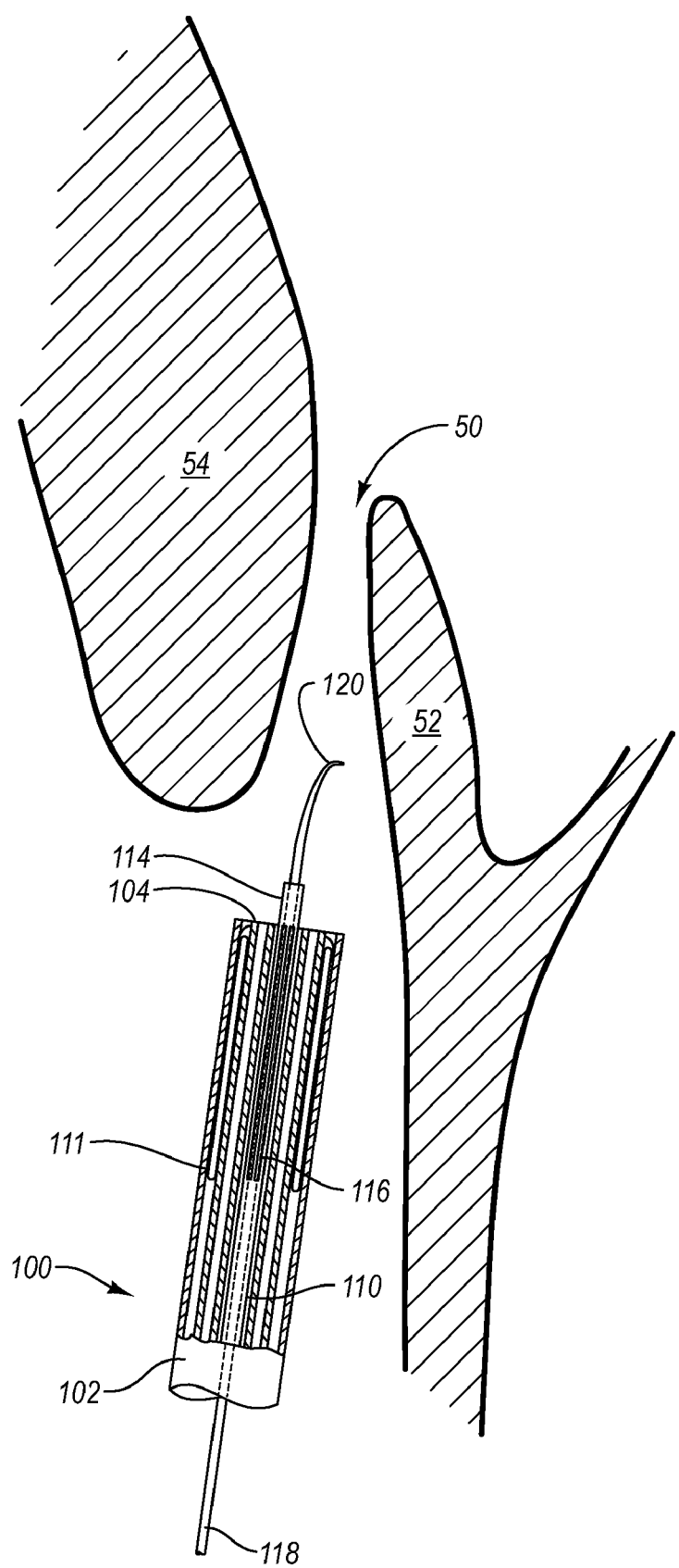
FIGS. 2A-2D illustrate a schematic representation of one embodiment of the medical device according to the present invention.
Figure 2B:
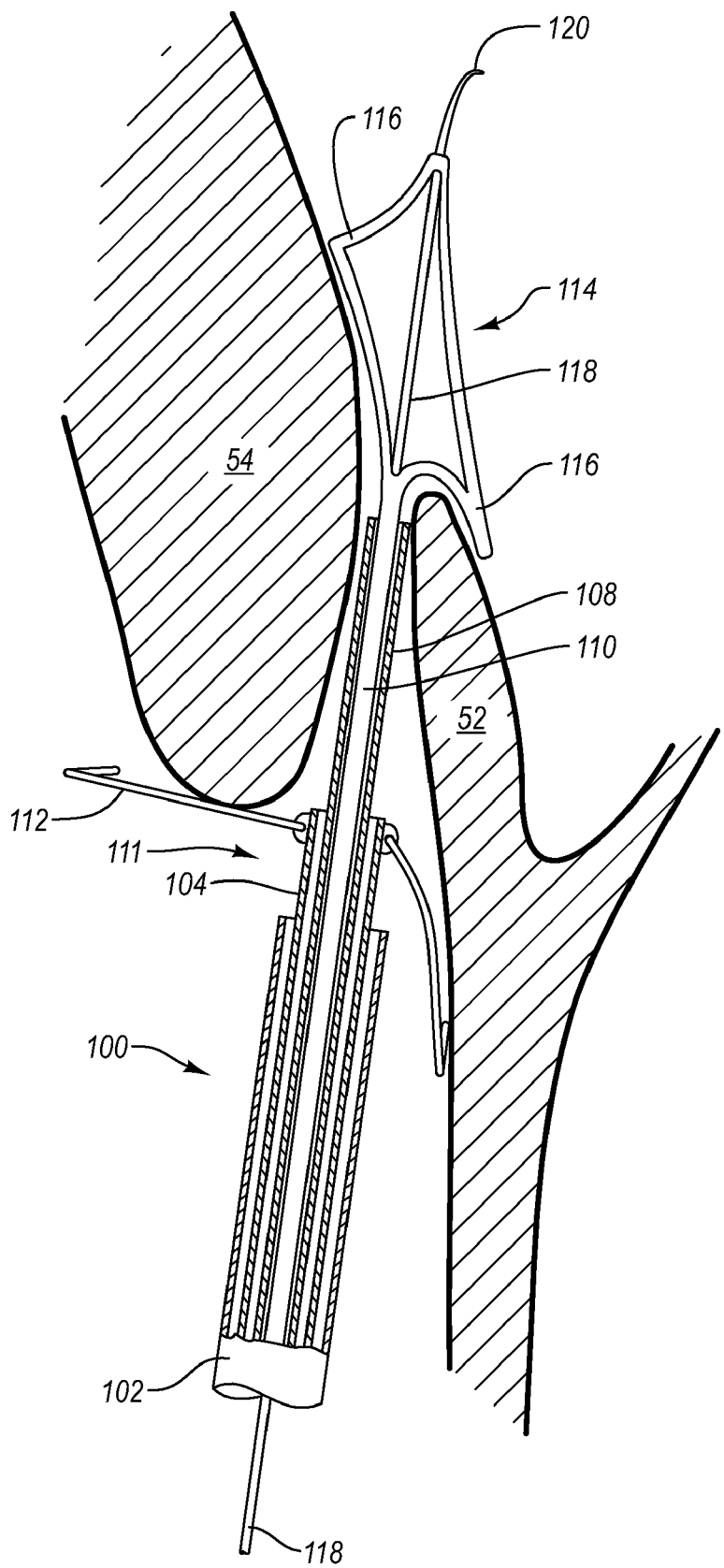

FIGS. 2A and 2B illustrate an exemplary, basic structure of a closure device 100; FIG. 2A illustrates the closure device 100 prior to deployment, while FIG. 2B illustrates the closure device 100 in position for application of radio frequency (RF) energy to close the tissue opening, such as the PFO. In the illustrated embodiment, closure device 100 can include a left electrode 114, with associated delivery shaft 110, a right electrode 111, with associated right electrode catheter 104, and a delivery sheath 102 configured to facilitate positioning of left and right electrodes 114, 111. A soft atraumatic tip 120 can be coupled to a distal end of left electrode 114 to facilitate placement of closure device 100 and to aid with passage of the closure device 100 through the tortuous anatomy of a patient. Optional insulation 108 can be provided on adjacent surfaces of delivery shaft 110 and/or right electrode catheter 104 to electrically isolate delivery shaft 110, and so the left electrode 114, from right electrode catheter 104, and so the right electrode 111.

In the illustrated embodiment, left electrode 114 can include one or more arms 116 coupled to or formed with a delivery shaft 110. An actuating shaft 118 is coupled to a distal end of left electrode 114 to facilitate deployment of one or more arms 116 after one or more arms 116, and optionally a portion of the delivery shaft 110, have been deployed from a right electrode catheter 104. The actuating shaft 118 can be moved proximally to allow the arms 116 to flex and form the left electrode 114 illustrated in FIG. 2B. Moving the actuating shaft 118 distally returns the arms 116 to the configuration illustrated in FIG. 2A. Actuating shaft 118 can be received and at least partially housed in delivery shaft 110, such that actuating shaft 118 is capable of movement, both rotational and translational, with respect to delivery shaft 110.

With continued reference to FIGS. 2A-2B, left electrode delivery shaft 110 can be received, and translated and/or rotated, within right electrode catheter 104. This again can aid with positioning the closure device 100 within the left atrium of the heart. As shown in the illustrated embodiment, the left electrode 114 can be inserted through the opening of the PFO 50. With transcatheter treatment of a PFO through the femoral vein and the inferior vena cava into the right and left atrium of the heart, it is advantageous for the closure device 100, including the delivery sheath 102, the right electrode catheter 104, and the left electrode 114, with the delivery shaft 110, to have a low crossing profile. It is further advantageous for the left electrode 114, including the delivery shaft 110, to have a low crossing profile to aid with passage through the PFO 50 into the left atrium. A low crossing profile enables the left electrode 114 of the closure device 100 to be withdraw through the small opening after the energy delivery and/or "tissue welding" have been accomplished.

Also associated with the closure device 100 is right electrode 111. As illustrated, right electrode 111 can include one or more arms 112 movably coupled to a right electrode catheter 104. These one or more arms 112 can be biased to open outwardly upon being deployed from within delivery sheath 102 and can be pivotally or hingedly attached or coupled to the right electrode catheter 104. Right electrode catheter 104 can receive left electrode 114 and delivery shaft 110 therein such that left electrode 114 and the delivery shaft 110 can translate and/or rotate in right electrode catheter 104.

For simplicity of discussion, only two arms 116 of left electrode 114 and two arms 112 of right electrode 111 are illustrated. However, it will be appreciated by one of ordinary skill in the art in view of the disclosure provided herein that left and right electrode 114 and 111 can include more than two arms 116 and 112. Additional information regarding left and right electrodes 114, 111 is disclosed with regards to FIGS. 3 and 10A, as well as in U.S. patent application Ser. No. 11/671,428, filed Feb. 5, 2007, the disclosure of which is hereby incorporated by reference in its entirety.

With continued reference to FIGS. 2A and 2B, delivery sheath 102 can be concentric with and substantially house right electrode catheter 104. When right electrode catheter 104 is extended from delivery sheath 102, right electrode 111 can be deployed so that arms 112 can extend to engage tissue adjacent or near the PFO 50 to facilitate physically closing the PFO 50 in connection with left electrode 114. When right electrode catheter 104 is withdrawn into delivery sheath 102, arms 112 can collapse and enter the right electrode catheter 104.

Delivery shaft 110 and left electrode 114, when not deployed, can be concentric with and substantially housed by right electrode catheter 104. As mentioned above, delivery shaft 110 can include insulation 108 on its exterior surface to provide electric insulation between right electrode catheter 104, right electrode 111, and conductive delivery shaft 110. Alternatively, insulation can be positioned on the interior surface of right electrode catheter 104. Furthermore, insulation can be positioned on both the interior surface of right electrode catheter 104 and the exterior surface of delivery shaft 110, or any combination thereof. Furthermore, as discussed more fully hereinafter, insulation can be strategically placed on left and/or right electrodes to focus RF energy as desired.

In the illustrated configuration, left electrode 114 and delivery shaft 110 form a continuous piece. However, it will be appreciated that left electrode 114 and delivery shaft 110 can form separate and distinct pieces being coupled together to perform the functions set forth herein. Movement of actuating shaft 118 relative to delivery shaft 110 can aid with deploying the left electrode 114. For instance, delivery shaft 110, with the coupled or formed left electrode 114, can be advanced into the left atrium 40 (FIG. 1A) and actuating shaft 118 moved proximally to deploy the arms 116, as illustrated in FIG. 2B. Once arms 116 are extended outwardly, delivery sheath 102 can be moved proximally to deploy right electrode 111. In this configuration, actuator shaft 118, with or without delivery shaft 110, can be moved to position the septum secundum 54 and septum primum 52 for tissue welding or closure of the PFO.

In an alternate configuration, the combination of right electrode catheter 104, delivery shaft 110, left electrode 114, and actuator shaft 118 can be advanced from within delivery sheath 102 to deploy and position the right electrode 111. With the right electrode 111 deployed, delivery shaft, with associated left electrode 114 and actuator shaft 118, can be advanced through the PFO 50. Again, with delivery shaft 110, and the coupled or formed left electrode 114, advanced into the left atrium 40 (FIG. 2A), actuating shaft 118 can be moved proximally to deploy the arms 116, as illustrated in FIG. 2B.

With the expandable configuration of the left electrode 114, a large surface area is provided through which RF energy can be passed. For instance, left electrode 114 can have an increased surface area outside right electrode catheter 104 than would otherwise be possible to insert in a patient. In other words, left electrode 114 of the present invention can be pushed out of and pulled back into a relatively small diameter right electrode catheter 104 and yet expand and have enough strength to hold the atrial walls together during energy delivery and substantially resist pulling through the PFO. Additional disclosure regarding left electrode will be discussed with regards to FIG. 3, and is disclosed in U.S. patent application Ser. No. 11/671,428, filed Feb. 5, 2007.

It will be understood in view of the disclosure provided herein that insulation 108 can be sized, configured and positioned such that some or all of the portions of the delivery shaft 110 that are in the PFO tunnel can delivery RF energy to the tissue in the PFO tunnel. In this manner, delivery shaft 110 can serve as an electrode, either independent from or in connection with left electrode 114, to facilitate delivery of RF energy to the PFO tunnel.

With arms 112 of right electrode 111 and arms 116 of left electrode 114 being positioned in this manner as illustrated, RF energy can be applied to the tissue which is between arms 112 and arms 116. The application of energy in this manner can cause tissue damage. Causing tissue damage in this manner can initiate tissue regrowth so as to weld the tissue together. After such treatment, actuating shaft 118 can be moved distally to move the one or more arms 116 radially inwardly in preparation for the delivery shaft 110, with associated left electrode 114, to be retracted back through the small remaining hole in the PFO. Thereafter, delivery shaft 110 can be withdrawn without substantially disturbing the weak "tissue weld" that has been created by the procedure.

Figure 2C:
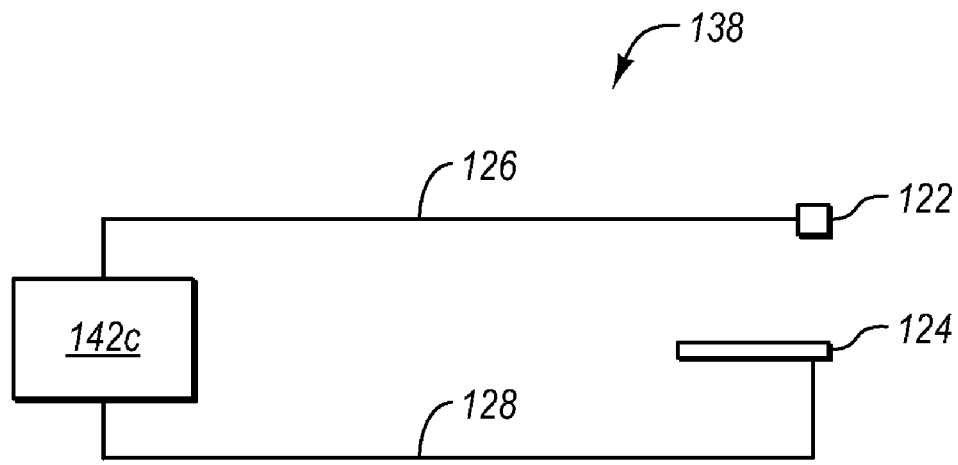
Figure 2D:
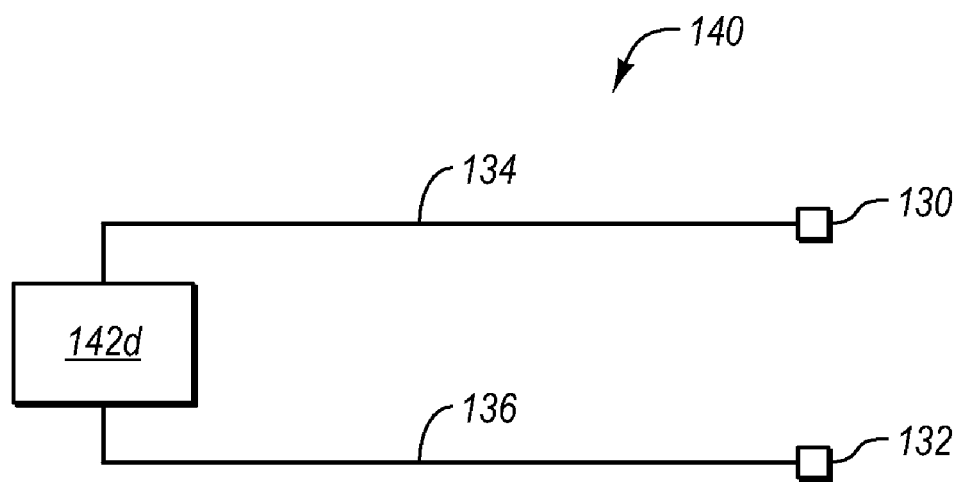

FIGS. 2C-2D illustrate general representations of a medical device operating in unipolar (FIG. 2C) and bipolar (FIG. 2D) modes. For example, FIG. 2C represents an electrode system 138 operating in unipolar mode, the system 138 including at least one electrode 122, such as a left electrode, right electrode, or other element which can serve as an electrode, in electronic communication with an RF generator 142c via an electronic coupling element 126, such as a wire or electronic cable. In unipolar mode, the system 138 includes a return electrode or ground 124. Ground 124 can be positioned on the patient's skin, or alternatively, can be a pad on which a patient rests. It will be understood that electrode 122 can include multiple electrodes which are electrically common elements, such that RF energy can be transferred from the electrodes 122 to the ground 124. The ground 124 can be electrically coupled to RF generator 142c by an electronic coupling element 128, such as a wire or electronic cable.

In bipolar mode, as illustrated in FIG. 2D, electrode system 140 can include a first electrode 130 electrically coupled to an RF generator 142d by an electronic coupling element 134, such as a wire or electronic cable, and a second electrode 132 electrically coupled to the RF generator 142d by an electronic coupling element 136, such as a wire or electronic cable. In this manner, RF energy can be passed between first and second electrodes 130, 132, rather than from the electrodes to a ground, as in the bipolar mode or configuration. It will be understood in view of the disclosure provided herein that first electrode 130, second electrode 132 and/or electrode 122 can include one or more electrically common electrodes.

Generally, medical grade metals, metal alloys, plastics, polymers, synthetics can be used to fabricate the closure device 100 and associated sheaths, electrodes, catheters, and tips. For instance, delivery shaft 110 and associated left electrode 114 can be fabricated from a shape memory material or superelastic material so that it can be formed to be biased in a tubular configuration, with the actuating shaft 118 being movable to overcome the biased configuration and deploy the one or more arms 116 to form the left electrode 114. Such shape memory materials can include, but not limited to NiTiNol. Other non-shape memory materials can also be used, such as but not limited to, stainless steel, steel, or other metals or metal alloys.

Delivery sheath 102 and right electrode catheter 104 can be fabricated from plastics, polymers, or synthetic materials having the desired flexibility characteristics. For instance, the materials used can include, but not limited to, Pebax, Polyimide, PTFE, Polyolefins, stainless steel braids, copper braids, molybedenum and thermocouple alloy conductors Right electrode 111 and left electrode 114 can be fabricated from conductive materials, such as steel, metal, or metal alloys to enable RF energy to be delivered to or near the PFO. Alternatively, right electrode 111 and left electrode 114 can fabricated from non-conductive materials, but coated with a conductive film or include a conductive members, such as a wire, ribbon, or the like to provide the conductive characteristics.

Additional disclosure regarding closure devices, their various structures and function, methods of use, methods of delivery and associated apparatus, electrodes, anchors, or related structures which can be used in connection with the present invention can be found and may be described in various co-pending patent applications, including U.S. patent application Ser. No. 10/964,311, filed Oct. 12, 2004, U.S. patent application Ser. No. 11/102,095, filed Apr. 8, 2005, U.S. patent application Ser. No. 11/534,996, filed Sep. 25, 2006, U.S. patent application Ser. No. 11/534,953, filed Sep. 25, 2006, U.S. patent application Ser. No. 11/671,428, filed Feb. 5, 2007, U.S. Provisional Patent Application No. 60/803,482, filed May 30, 2006, U.S. Provisional Patent Application No. 60/809,524, filed May 31, 2006, and U.S. patent application entitled "METHODS, SYSTEMS, AND DEVICES FOR SENSING, MEASURING, AND CONTROLLING CLOSURE OF A PATENT FORAMEN OVALE" (Attorney Docket No. 16348.23.1.1), filed May 29, 2007, the discloses of which are hereby incorporated by reference in their entirety.

The temperature profile in the tissue surrounding the PFO during RF heating can be affected by the geometry of the electrodes 111 and 114. Electrodes 111 and 114 may be operated in either unipolar or bipolar mode. In a unipolar system, the current flows from the active electrode near the tissue to be heated to a return electrode, for example, on the patient's skin (not shown). Either or both of the electrodes 111 and 114 can be operated in unipolar mode. In bipolar RF heating, the current flows between two active electrodes in the area to be heated. Unipolar RF heating results in non-uniform heating that is highest next to the electrode because the current density rapidly decreases as the current spreads out in the body as it travels toward the return electrode. Bipolar heating can provide a more uniform current density and heating because the current path is from one electrode to the other. In a bipolar system, higher current densities and resulting higher heating rates can occur in areas where the distance between bipolar electrodes is smaller.

Figure 3:
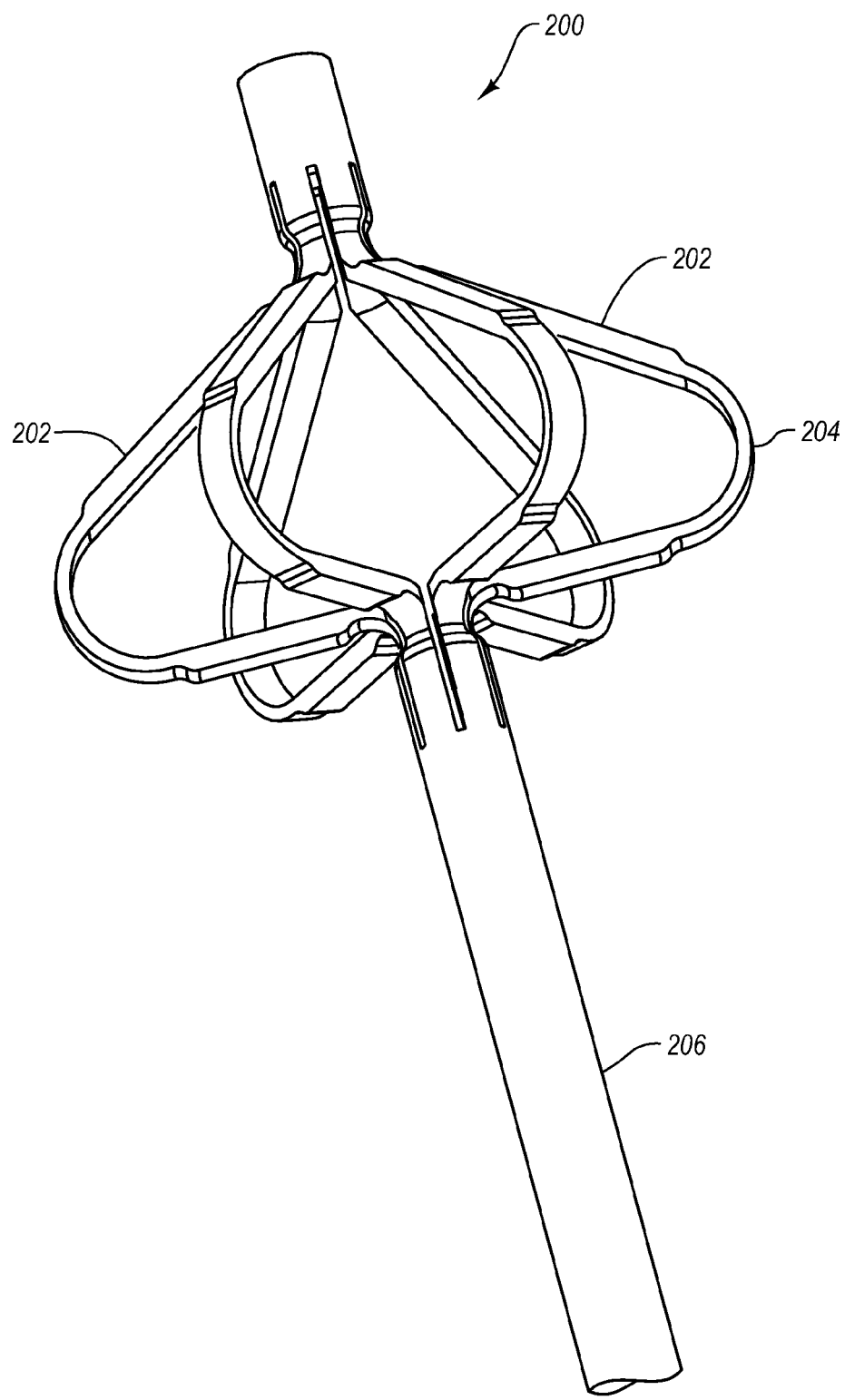
FIG. 3 illustrates a schematic representation of one embodiment of a left atrial anchor of the medial device of the present invention.

Heating using RF energy can be preferentially focused on a desired location, such as in the tunnel area of the PFO. Focused heating can be accomplished by utilizing bipolar electrodes having higher conductor density in locations that correspond with focused tissue areas. FIG. 3 illustrates an exemplary embodiment of an anchor or electrode 200 which can be utilized in connection with preferential heating. In one embodiment, electrode 200 can be left electrode 114, as described with respect to FIG. 2. Details regarding electrode 200 can be found and are disclosed in pending U.S. patent application Ser. No. 11/671,428, filed Feb. 5, 2007, which has been incorporated herein by reference. For example, electrode 200 can be configured to have a pattern of radial spokes or arms 202. As the distance between spokes 202 increases toward the perimeter 204 of the electrode, the conductor density decreases which decreases current density and heating. Heating may be further accentuated in the tunnel area of the PFO by utilizing a conductive shaft 206 configured to traverse the tunnel area of the PFO, wherein the shaft 206 is one of the heating signal poles in a bipolar electrode system.

More uniform heating may be achieved by insulating at least a portion of shaft 206 and by selectively insulating parts of the right and/or left electrodes, such as electrodes 111 and 114, in order to achieve a more uniform conductor density. Portions of delivery sheath 102, right electrode catheter 104, and/or delivery shaft 110, may be insulated by polymeric coatings such as epoxy, acrylic, silicone, urethane, and parylene. Conductive portions of the electrodes 111 and 114 that are not designed to contact the atrial wall may be insulated to prevent unintended heating of other cardiac structures and blood. Another electrode arrangement that concentrates heating in the tunnel is to include a separate electrode that traverses the tunnel and that acts as one pole with both the right and the left atrial anchor/electrodes connected to another pole. Another topology that results in high tunnel heating concentration is operating the left electrode in unipolar mode when delivery shaft 110 serves as an electrode and RF energy can be delivered from delivery shaft 110.

Changing the mode of operation of the left and right electrodes can effect the heating and treatment of the PFO. For example, operating the left and right electrodes between unipolar and bi-polar modes, as well as modifying the duration and/or power level of each application of RF energy, can effect the treatment of the PFO. More than one mode of operation may be used within one thermal treatment to tailor the temperature distribution in the tissue surrounding the PFO.

Figure 4:
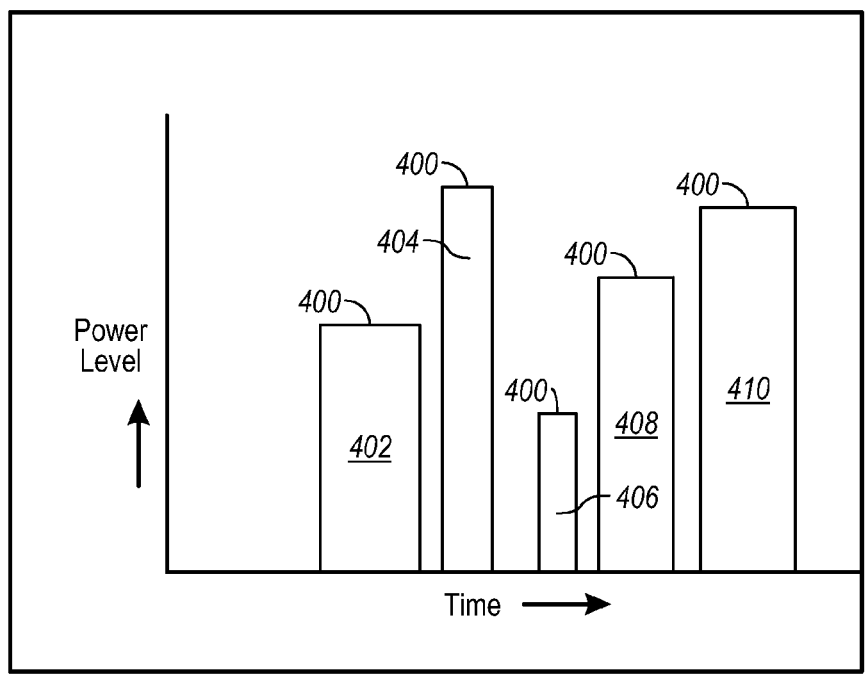
FIG. 4 illustrates a graphical representation of operating electrodes to treat an internal tissue opening.

The system of electrodes (i.e., left electrode, right electrode, and an external ground electrode) can change modes at a high rate in order to achieve heat distributions that are not possible with a single mode or connection. For example, FIG. 4 illustrates a portion of an exemplary treatment having multiple RF energy applications 400, illustrating the changes in mode, duration and power level of the right and left electrodes between RF energy applications 400. In the illustrated embodiment, a first RF energy application 402 can include right anchor/electrode operating in unipolar mode for a certain duration, such as few milliseconds, at a certain power level, and then a second RF energy application 404 can include left anchor/electrode operating in unipolar mode for a duration shorter than the first RF energy application 402, but at a higher power level than the first RF energy application. In a third RF energy application 406, right and left electrodes can be operated in bipolar mode for a duration and at a power level less than either of the first and second RF energy applications 402, 404. In a fourth RF energy application 408, right anchor/electrode can operate in unipolar mode and in a fifth RF energy application 410, right anchor/electrode can operate in unipolar mode again at a higher power level and longer duration than in the fourth RF energy application 408, for example.

It will be appreciated by one of ordinary skill in the art in view of the disclosure provided herein that a variety of sequences can be utilized without departing from the scope and spirit of the invention. For example, the modes, patterns, duration and power levels can be modified. Furthermore, sequences can be repeated for the duration of a treatment or the sequence may be altered during the treatment so that the unipolar mode parts of the sequence are favored at the start of the heating cycle and the bipolar mode parts of the sequence are favored toward the end of the cycle. Many different sequences of modes and connections are possible, each with unique spatial and temporal heat distribution patterns.

The heat profile in the tissue can also be a function of the degree of electrical contact between the electrode and the tissue. Anchor/electrodes that are relatively rigid may make contact with the tissue only at high points such as the inferior aspect of the septum secundum. This may cause locally high current densities and heating. More conformal electrodes will give more uniform current densities and heating. It can be desirable to include separate electrodes coupled to the anchors. Separate electrodes could be very soft and conformable since they do not also need to support the device.

It can be desirable for a PFO closure device to mechanically, as well as thermally, accommodate the variety of PFO morphologies. It is an optional objective of the device of this invention to minimally distort the anatomy of the PFO while clamping it closed during tissue welding, or in other words, during application of RF energy. In order to accommodate PFOs with varying tunnel lengths and septal thicknesses, the distance between the right and left anchor/electrodes may be variable.

One method of setting this distance is to visualize the device in the PFO via fluoroscopic and/or ultrasonic imaging and set this distance manually. Due to the limitations of these imaging systems, it can be desirable to have a device which automatically sets the anchor/electrode spacing. This can be accomplished by a mechanism that urges the anchor/electrodes toward each other with a predetermined force that is relatively constant over a desired range. With the proper amount of force, the anchor/electrodes can move toward each other until their movement is limited by the atrial tissue that is lightly clamped between them. There are several methods of accomplishing this function, which can be used independently or in combination with other devices.

The configuration of FIGS. 2A and 2B can urge the electrodes 111 and 114 toward each other with a desired and optionally pre-determined force that is relatively constant over the desired range. With the proper amount of force, the electrodes 111 and 114 can move toward each other until their movement is limited by the atrial tissue that is clamped between them. For instance, movement of delivery shaft 110 relative to right electrode catheter 104 can apply force to move the septum secundum 54 and septum primum 52 toward each other. Alternatively, and/or in combination with the above, movement of actuating shaft 118 with respect to right electrode catheter 104 can move left electrode 114 to provide the desired force.

Figure 5:
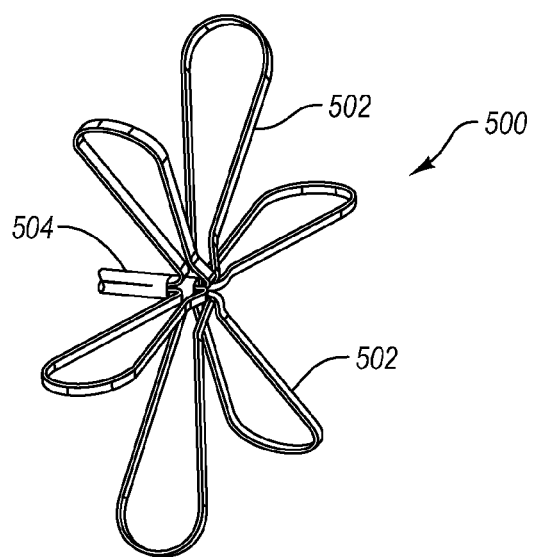
FIG. 5 illustrates a schematic representation of one embodiment of a compliant right atrial anchor of the medial device of the present invention.

In another configuration, maintaining relatively constant force between the anchor/electrodes can be achieved through constructing the electrodes such that they have axial compliance in their structure. Either the right anchor/electrode or the left anchor/electrode or both may have this characteristic to accomplish this goal. For example, FIG. 5 illustrates one embodiment of a right anchor 500 having one or more compliant arms 502 linked to a delivery shaft 504. Compliant arms 502 can be sized and configured to provide axial compliance as arms 502 contact and engage tissue. Furthermore, arms 502 can be linked to shaft 504 in a manner that enables each arm 502 to move independently from another arm 502, thus enabling right anchor 500 to better conform to the tissue adjacent the PFO. It will be understood that delivery shaft 110 can extend through a portion of the right anchor 500 as discussed previously.

Figure 6:
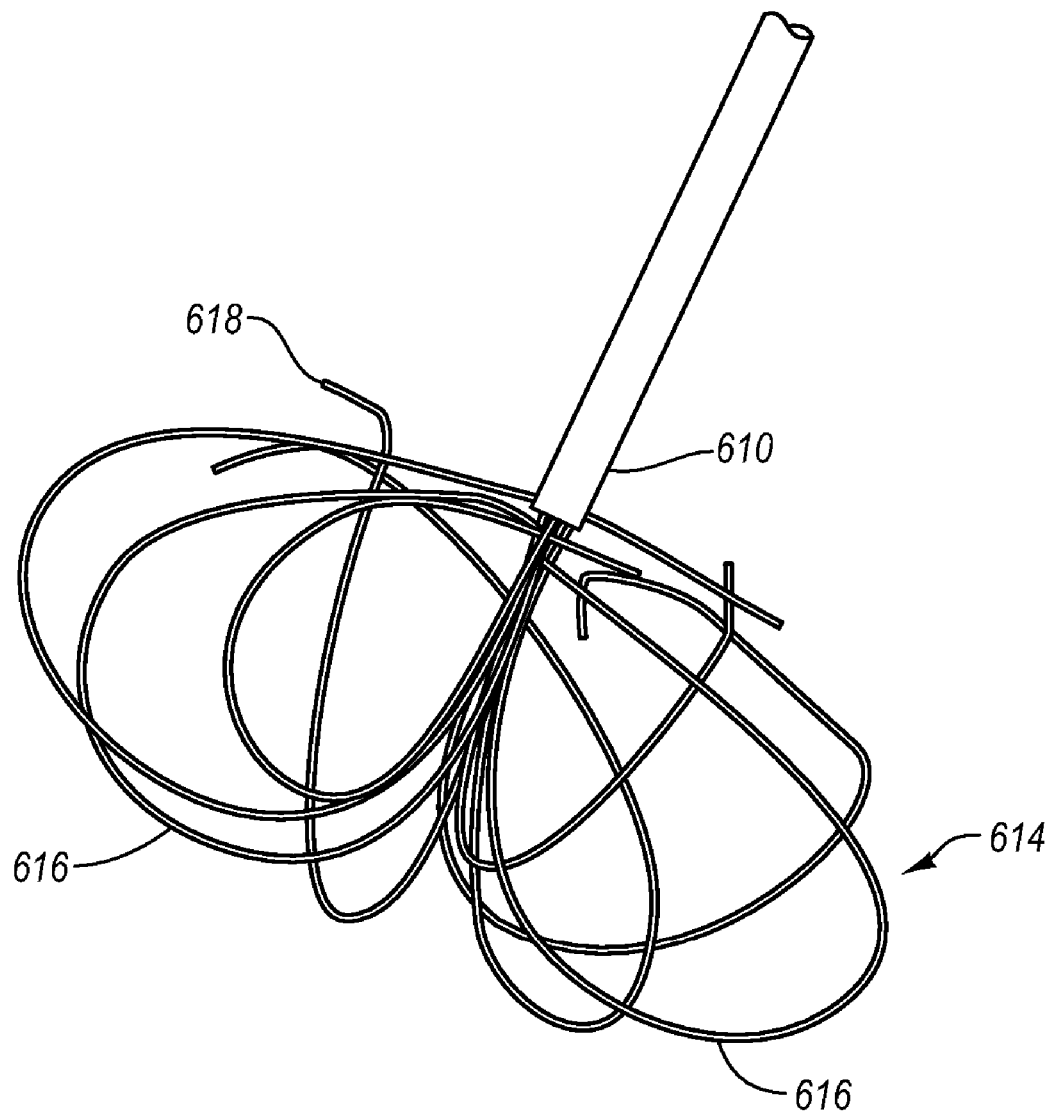
FIG. 6 illustrates a schematic representation of one embodiment of a compliant left atrial anchor of the medial device of the present invention.

FIG. 6 illustrates one embodiment of a left anchor/electrode 614 having one or more compliant arms 616. In the illustrated embodiment, instead of being coupled to or formed with the delivery shaft 610, the left anchor/electrode 614 can be slidably received within delivery shaft 610 having a generally uniform cross-section along its length. Left electrode 614 of the present invention can be pushed out of and pulled back into delivery shaft 610 with a diameter of about 1 mm, for example, and yet expand to a diameter of about 20 mm, for example, and have enough strength to hold the atrial walls together during energy delivery and strongly resist pulling through the PFO. It will be understood, that the configuration of FIGS. 2A-2B can incorporate left anchor/electrode 614, and can include another delivery tube or shaft within which delivery shaft 610 can be received and from which it can be deployed.

With continued reference to FIG. 6, the left anchor/electrode 614 can be deployed from within delivery shaft 610 through distal movement of arms 616, proximal movement of delivery shaft 610, or a combination of movement of both of arms 616 and/or delivery shaft 610. The arms 616 are biased to the illustrated configuration. The arms 616 can be fabricated from NiTiNol, other shape memory or superelastic material, or other sufficiently flexible material, such as stainless steel or plastic, to enable the arms 616 to move to the configuration illustrated in FIG. 6 upon deployment of the arms 616. As illustrated, the plurality of arms 616 can be slidably received within the delivery shaft 610. A distal end 618 is movable out of a distal end of the delivery shaft 610, while the proximal end (not shown) can be slidably received within the delivery shaft 610 or coupled to delivery shaft 610, such that movement of delivery shaft 610 causes movement of arms 616. Arms 616 can be sized and configured to provide axial compliance as left anchor 614 is pulled back from the left atrium and arms 616 contact and engage the tissue adjacent the PFO. Additional disclosure regarding compliant electrodes, including structural disclosure and methods of use and delivery, can be found in co-pending U.S. patent application Ser. No. 11/534,953, filed Sep. 25, 2006, which has been incorporated by reference herein.

Another way to maintain a relatively constant force between the anchors/electrodes is to provide tension or compression spring(s), such as a spring having a relatively low spring constant for example, adjacent to the anchor/electrodes to urge the anchors/electrodes towards each other. FIGS. 7A-7E illustrate various embodiments of the invention which incorporate a biasing member, such as one or more springs, to provide desired compression characteristics.

Figure 7A:
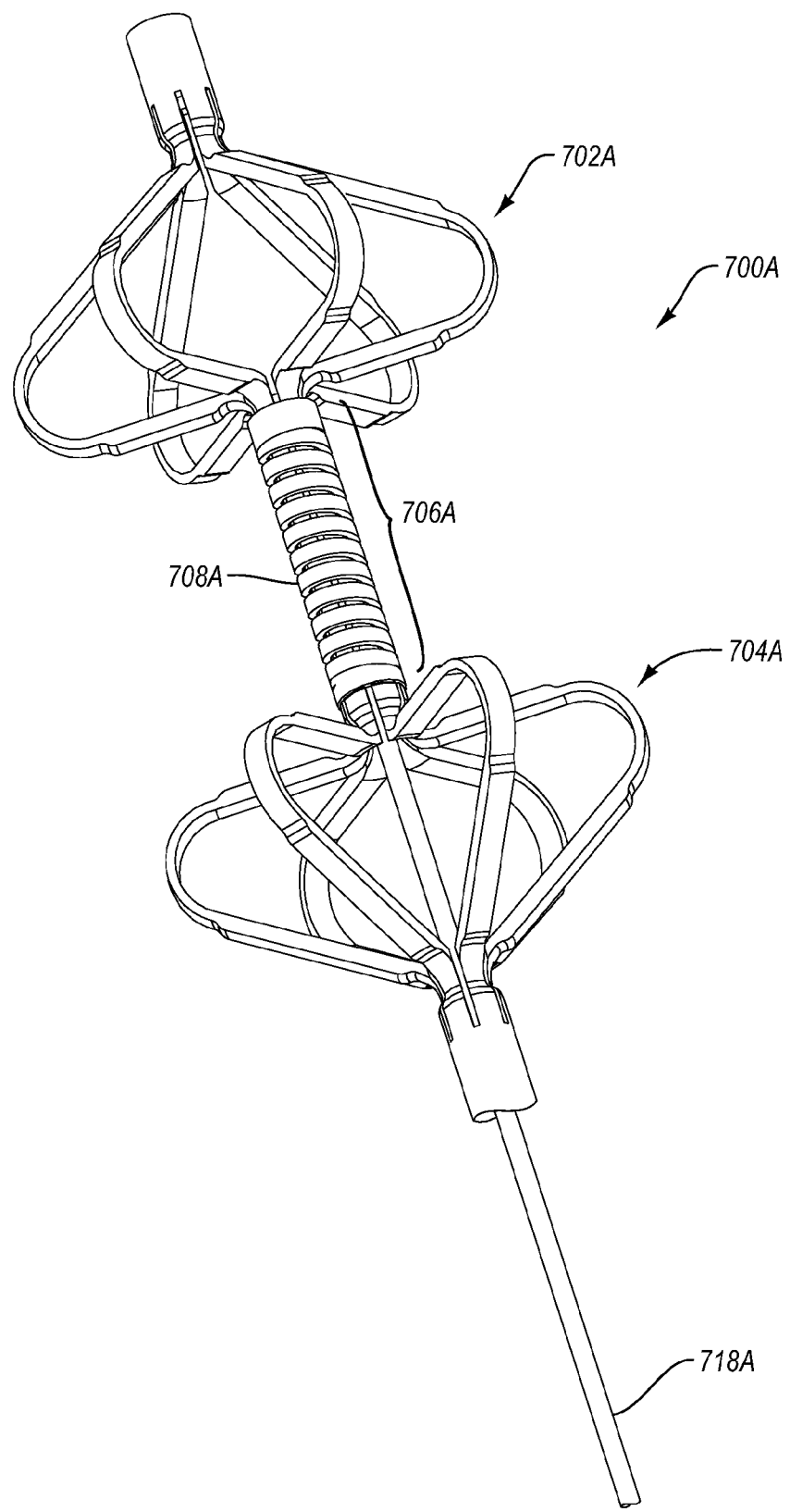
FIGS. 7A-7E illustrate schematic representations of embodiments of a medical device, including a biasing member, of the present invention.

FIG. 7A illustrates one embodiment of a medical device, such as a closure device, having a left electrode similar to the left electrode 114 disclosed with regards to FIGS. 2A-2B, which can apply desired compression forces in a controlled manner to aid with closure of the PFO. FIGS. 7B-7E illustrate general or basic structures of medical devices that can also provide desired compression capabilities or characteristics. It will be understood that the principles disclosed with regards to FIGS. 7A-7E can be incorporated into a variety of different shapes and designs of electrodes disclosed herein and/or disclosed in the references incorporated herein by reference.

As mentioned herein, it can be desirable to apply a force to close the septum in a controlled manner to limit the maximum "clamping" or closing force applied to the septum as a PFO is pulled closed in preparation for a thermal or other treatment to close the PFO. FIG. 7A illustrates one embodiment of a medical device 700a having a left electrode 702a linked to a right electrode 704a by a compliant section 706a formed from a spring, coil, or other axially compliant element 708a. The compliant section 706a, such as the axially compliant element 708a, can be used to limit the peak forces applied to the septum so as to not damage the septum or distort the PFO independent of the force applied by the doctor to pull the two electrodes together. The compliant element 708a can be located between left and right electrodes 702a, 704a, or at other locations, such as opposite sides of the electrodes. In the illustrated configuration, the left electrode 702a and right electrode 704a can be mirror images of each other and can be actuated using an actuating shaft 718a in a similar manner to that described with respect to FIGS. 2A and 2B, i.e., movement of the actuating shaft 718a in either the proximal or distal directions to deploy or retract the electrodes having arms biased to extend outwardly or along the longitudinal axis of the closure device 700. Additional information regarding medical device 700a is disclosed in U.S. patent application Ser. No. 11/671,428, filed Feb. 5, 2007, which has been incorporated by reference herein.

In FIGS. 7B-7E, basic structures of different closure devices are disclosed for simplicity. In the illustrated embodiments of FIGS. 7B-7E, the closure device or medical device 700 can include a first anchor 702, a first delivery shaft 704 operatively associated to first anchor 702, a second anchor 706 movable with respect to first anchor 702, a second delivery shaft 708 operatively associated to the second anchor 706, and a biasing member 710. Specific details about first and second anchors, and first and second delivery shafts can be obtained by the disclosure provided herein and in the incorporated references, with regards to anchors, electrodes, delivery tubes and delivery shafts. It will be understood that the anchors can also be considered an electrode, i.e., RF energy can be passed through the anchor to aid with closing the lumen within which the closure device 700 is disposed.

Figure 7B:
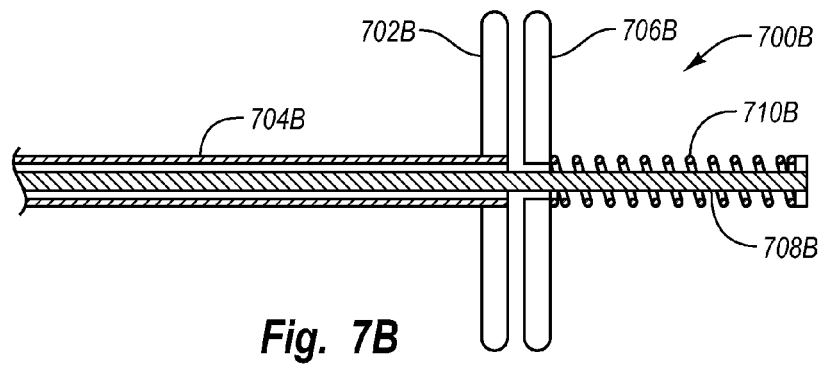
Figure 7C:
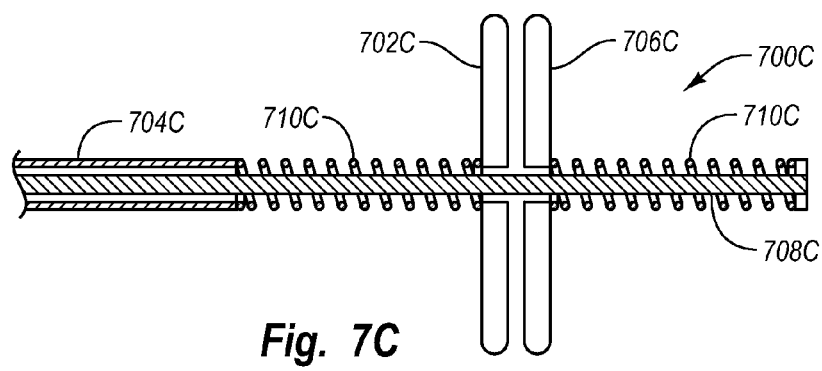
Figure 7D:
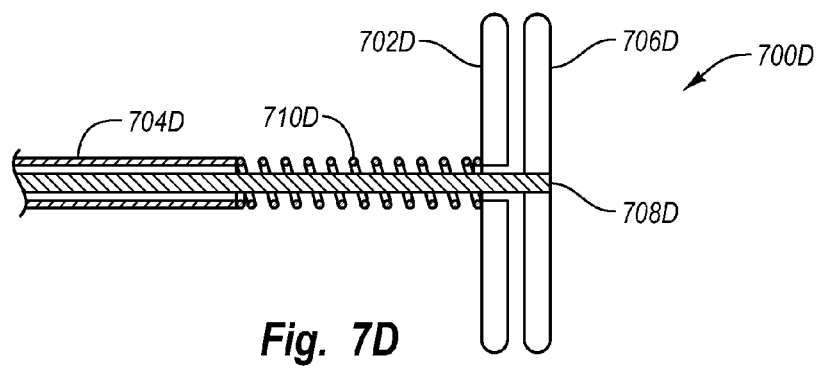

In FIG. 7B, medical device 700b includes biasing member 710b extending from second delivery shaft 708b to second anchor 706b. In this manner, as medical device 700B is positioned in relation to a PFO, as illustrated in FIGS. 2A-2B, movement of second delivery shaft 708b in the proximal direction can enable engagement of second anchor 706b with the tissue without applying excess amounts of force to the tissue. Likewise, FIG. 7C illustrates two biasing members 710c extending to first anchor 702c and second anchor 706c, respectively. In this manner, as first delivery shaft 704c is moved in the distal direction and second delivery shaft 708c is moved in the proximal direction, biasing members 710c can absorb some energy thereby reducing the risk of applying excessive pressure to the PFO for closure. FIG. 7D illustrates biasing member 710d extending from first delivery shaft 704d to first electrode 702d.

Figure 7E:
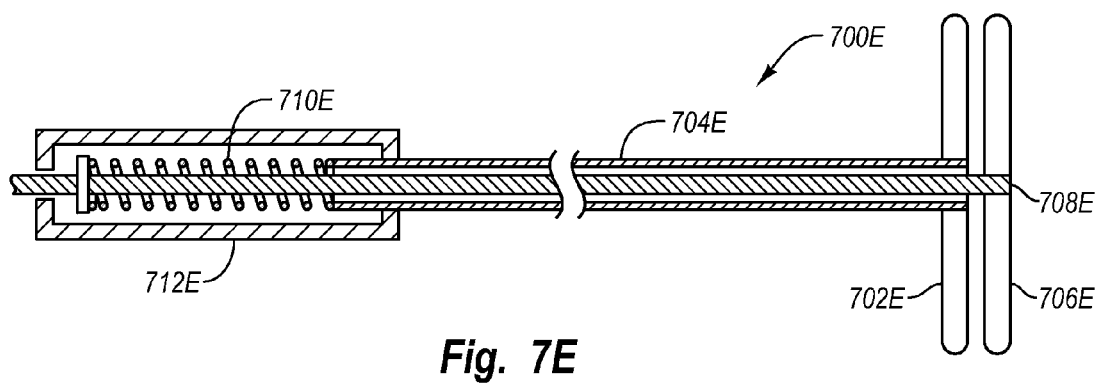

FIG. 7E illustrates medical device 700e having a handle 712e coupled to first delivery shaft 704e, and biasing member 710e extending from first delivery shaft 704e to second delivery shaft 708e. In this manner, as second delivery shaft 708e is moved distally with respect to handle 712e, and thus with respect to first delivery shaft 704e, the distance between first anchor 702e and second anchor 706e increases. Medical device 700e can be configured such that the distance between first anchor 702e and second anchor 706e is slightly less than the PFO tunnel. In this manner, in order to position second anchor 706e in the left atrium when first anchor is positioned adjacent the PFO in the right atrium, a user could compress the biasing member or spring 710e. Once in place, second anchor 706e would be forced against the tissue of the PFO in the left atrium by biasing member 710e, thereby providing a clamping or pinching force to reduce the size of the PFO.

As described above, the medical device 700e of the present invention includes handle 712e configured to enable a user to move the first and second anchors/electrodes 702e and 706e relative to each other. It can be understood that one or more handles can be used to move first and second electrodes 702e and 706e. For example, a first handle can be linked to the first anchor/electrode and a second handle can be linked to the second anchor/electrode, such that movement of the first handle causes movement of the first electrode and movement of the second handle causes movement of the second electrode. An optional travel stop in the handles can be utilized to limit relative movement between the two handles to something less than would be required to completely compress or extend the spring element positioned between the two anchors/electrodes 702e and 706e. In that situation, the spring would be selected to exert a desired force or range of forces to the clamp or hold the portions of the PFO or other portion of the body.

As illustrated in FIG. 7E, the biasing member 710e, such as a spring, or force controlling compliant element can be found in the handle 712e used by the physician to manipulate the medical device 700e. In this embodiment, the biasing member 710e can be interposed between the handle the physician manipulates and the catheter connections to the anchors/electrodes 702e and 706e inside the patient. An optional travel stop (not shown) between the left and right handles can substantially prevent the anchors/electrodes 702e and 706e from moving, relative to each other, farther than a desired maximum distance. When the travel limit is reached, the spring element can impose a desired pushing or pulling force on the connections to the anchors/electrodes 702e and 706e.

It can also be desirable to not distort the position or shape of the septum or clamped PFO between the anchors/electrodes 702e and 706e by excessive pulling or pushing. The external handle 712e and associated operating mechanism can be designed to allow the left and right anchors/electrodes 702e and 706e to float axially individually and/or as a pair to allow the septum to rest at its neutral position. This can occur when the two anchors/electrodes 702e and 706e are exerting a clamping force to close the PFO.

It will be appreciated by one of ordinary skill in the art in view of the disclosure provided herein that the biasing member can be implemented on either the right or the left anchor/electrode or on both. In one embodiment, the biasing member, such as a spring, can be preloaded so that the desired force is achieved when the anchor/electrodes are together. If the biasing members have a relatively low spring constant, the force urging the anchor/electrodes together does not change appreciably when they are separated by distances that cover the range of PFO tunnel lengths and septal thicknesses.

Alternatively, the biasing members, such as one or more low spring constant springs that urge the slidably disposed anchors toward each other, may be located in the handle unit at their proximal end which is outside the body. In this embodiment, the springs act on the delivery shafts, catheters, or tubes that are connected to the anchors or electrodes. The shafts, catheters, or tubes which are slidably disposed to each other may have PTFE or other low friction sliding surfaces to allow the forces to be transmitted to the anchor/electrodes with minimal frictional losses.

In addition to anchor/electrode clamping force control, there are a number of other features of the present invention that can enable treatment of a PFO while reducing the distortion of the PFO from its natural geometry. Other features of the device that provide this anatomical conformance can include the ability of the right and left anchor/electrodes to freely pivot and/or flex relative to their delivery shafts, catheters, or tubes. Flexure can enable the anchor/electrodes to be positioned against the atrial wall in an optimal manner, which, in general, may not be perpendicular to the axis of the delivery shaft. An additional feature can include the ability of the arms of the right and left anchor/electrodes to move independently and adapt to non-planar surface topology to seek optimal contact with the atrial wall. Yet another feature can enable the ability of the delivery shafts of the right and left anchor/electrodes in the area just proximal to the PFO to freely pivot or flex. This allows the shafts to assume the shape required by the pathway from the inferior vena cava and through the PFO without substantially altering the orientation of the PFO.

Additionally, adequate flexibility of the delivery shafts can also enable the patency of the PFO to be evaluated after treatment but prior to device removal without high risk of tearing open the just-welded flaps. The patency can be evaluated by any of the methods discussed in this disclosure with the clamping force removed and the anchor/electrodes moved apart, but with the left anchor/electrode shaft, catheter, or tube remaining in the PFO tunnel. If residual patency is detected, further treatments can be administered without the difficulty of re-crossing the PFO.

Figure 8A:
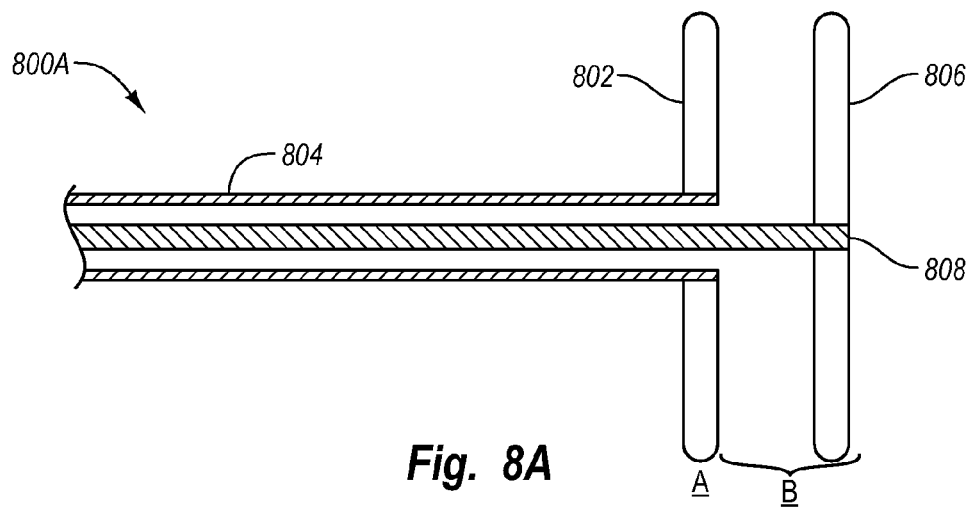
FIGS. 8A-8C illustrate schematic representations of embodiments of a medical device of the present invention.
Figure 8B:
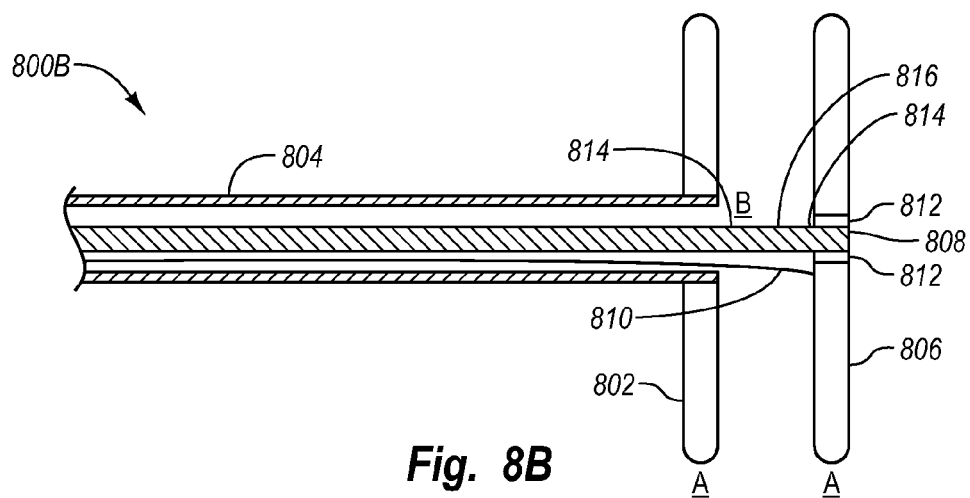
Figure 8C:
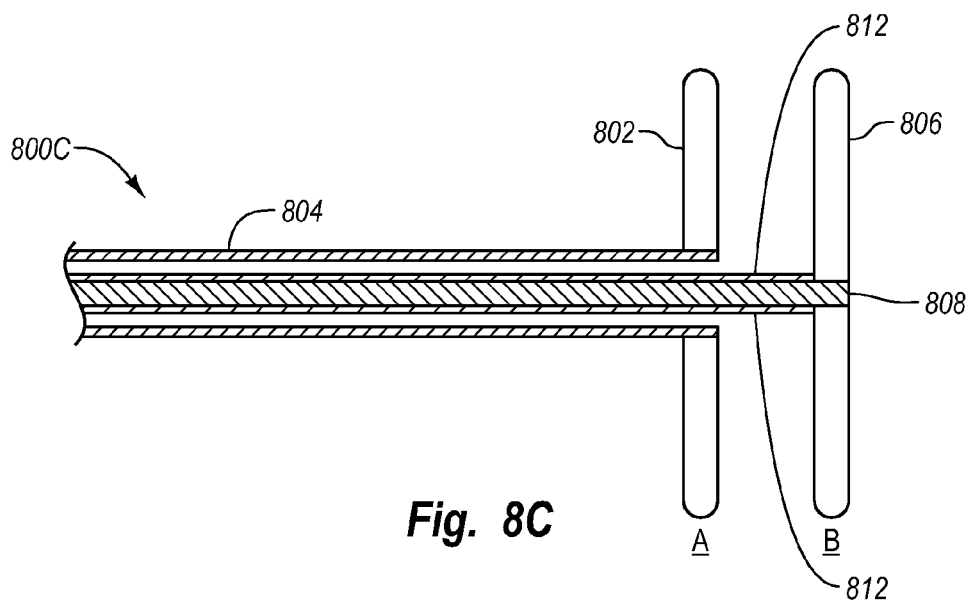

FIGS. 8A-8C illustrate exemplary embodiments of another closure device or medical device 800. While the illustrations in FIGS. 8A-8C are very general for simplicity, it is intended that these principles can be applied to the electrode and/or anchor configurations disclosed herein or in the disclosures of the references incorporated herein. Generally, medical device 800 can include a right anchor 802, a right anchor delivery shaft 804 coupled to right anchor 802, a left anchor 806 and a left anchor delivery shaft 808. In FIGS. 8A-8C, electrically common elements forming electrodes are labeled "A" and "B" respectively, even when physically separate.

FIG. 8A illustrates one embodiment of the present invention wherein right anchor 802, left anchor 806 and left anchor delivery shaft 808 each form an electrode, the left anchor 806 and left anchor delivery shaft 808 being electrically common elements, identified as "B". This configuration concentrates heating or energy at the center of the right electrode 802 where the distance to left anchor delivery shaft 808 is less than to left anchor 806. Energy density decreases as the distance from the right electrode 802 increases.

FIG. 8B illustrates another embodiment of the present invention. In this configuration, right anchor 802, left anchor 806 and left anchor delivery shaft 808 each form an electrode, with left anchor 806 and right anchor 802 being electrically common elements, identified as "A". In this embodiment, medical device 800 can further include an insulator 812 positioned between left anchor 806 and left anchor delivery shaft 808, and a electrical connector 810 coupled to left anchor 806. Insulator 812 can be configured to provide a desired amount of RF energy insulation between left anchor 806 and left anchor delivery shaft 808. This insulator 812 can be a dielectric coating or element, such as a ceramic or polymeric hub or sleeve, or other non-conductive material to electrically isolate left anchor 806 from delivery shaft 808. Electrical connector 810 can be configured to enable left anchor 806 to be electrically common with right anchor 802. Electrical connector 810 can include conductive metal wires, braids, conductive metallization layers, a spring or springs, flexible circuits, or other electrical connection means. Copper, stainless steel, molybdenum, silver, gold, and various conductive metal alloys may be used for the wires and/or metalizations. Furthermore, electrical connector 801 can be any means of making the desired electrical connection between left anchor 806 and right anchor 802. This connection path may occur near the distal end of the medical device 800B, the proximal control handles (not shown), or anywhere in between.

In this configuration, when medical device 800 is positioned in the PFO, energy can be concentrated at both ends of the tunnel and can decrease toward the center of the tunnel. For example, energy can be concentrated at concentration points 814 on left anchor delivery shaft 808 and can decrease towards a center portion 816 on left anchor delivery shaft 808.

FIG. 8C illustrates another embodiment of the present invention wherein right anchor 802 and left anchor 806 each form an electrode. In the illustrated embodiment, medical device 800 can include insulation 812 positioned on left anchor delivery shaft 808. This configuration can be desirable because it can tend to produce uniform heating along the length of the tunnel without a very short energy flow path to the portion of the left anchor delivery shaft 808 next to the anchors 802, 806.

Reference has been made herein to spaced apart structures that function as electrodes. For instance, in FIGS. 8A-8C electrode 806 is spaced apart from electrode 802. It can be understood, however, that in other configurations the electrode can be formed from one or more pairs of alternating electrodes or conductive portions disposed relative to each other in a desirable pattern on one or more anchors and/or delivery shafts. For instance, an anchor or delivery shaft, catheter or tube can be formed into an electrode by the inclusion of conductive portions. Such patterns can be formed along an axis, in concentric rings, interleaved fingers, parallel lines or curves, or in other desired spatial relationships or configurations. The electrodes or conductive portions can be arranged to create pairs of relatively short, lower impedance paths between electrodes or conductive portions where the energy flow is be concentrated.

The shape or length of each pair, the number of pairs, the spacing between pairs, and their spatial relationship can be varied, resulting in energy density distributions tailored and configured as desired. The size and configuration of these electrodes or conductive portions can be applied to all configurations of electrodes or anchors disclosed herein, not just to axially arranged ones. Furthermore, electrodes or conductive portions can be configured to operate as unipolar or bipolar electrodes. Such paired electrode sets can be configured to be coupled to or form a part of the elements of the medical device, such as atrial anchors, for example, whose purpose is to clamp the PFO closed while energy is delivered. In a different example, a clip or implantable closure device can be utilized to clamp the PFO closed, the clip or implantable closure device can be moved through a tortuous path and can have electrode pairs distributed thereupon.

Figure 9A:
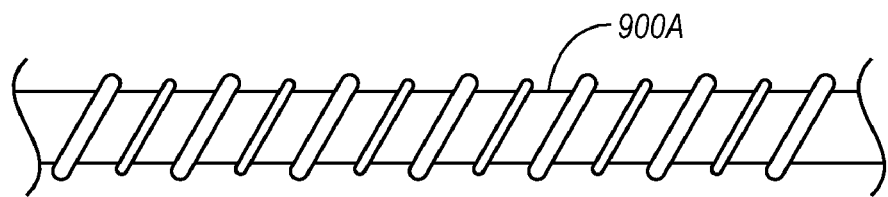
FIGS. 9A-D illustrate schematic representations of embodiments of a medial device of the present invention.

FIGS. 9A-9D illustrate general embodiments of an element 900 having a first electrode 902 and a second electrode 904 associated therewith in accordance with the above. It will be understood that element 900 can be an anchor, a delivery shaft, an arm of an anchor, or any other structure of the medical devices disclosed herein or in the disclosures incorporated herein by reference. FIG. 9A illustrate one embodiment of the present invention in which first and second electrodes 902, 904 wrap around a central axis in a spiral fashion along the length of the axis. Electrodes 902, 904 can be made from Kapton film with conductors on its surface or interior. Such conductors might also be arrayed with temperature sensors made in the same way (on the same or separate film) so that temperature sensors could be arrayed along the electrode for use in sensing tissue temperature.

Figure 9B:
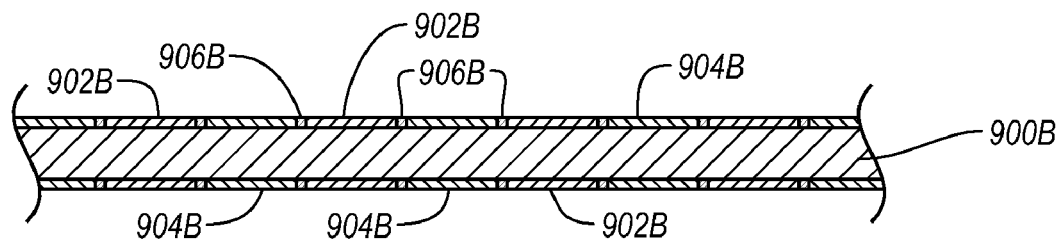

FIG. 9B is a cross-sectional view of an alternative embodiment of the present invention in which a substantially axial electrode 900b can be formed by placing alternating conductive and insulating tubes along an element 900b. For example, first electrode 902b and second electrode 904b can be wrapped around element 900b and separated by an insulator 906b. First and second electrodes 902b, 904b can be wrapped completely around element 900b, can be partially wrapped around element 900b, or some combination thereof. In a simple axial electrode, pairs of conductors can be alternated at various lengths, spacing, and number to achieve desired energy delivery. A set of such axial electrodes properly arranged, may be joined with one or more other electrodes to distribute energy in a PFO tunnel. In this manner, electrode pairs can deliver energy doses more evenly spread along the length of a PFO. For example, one or more such substantially axial electrode sets could be inserted through a PFO to deliver energy inside the PFO tunnel. The electrode pairs can also be deployed external to the tunnel to heat other surfaces. The electrode pairs can also be used to penetrate into tissue and heat along their length while disposed inside the tissue. For example, a pair of axial or curved electrodes can be coupled with spreading rods, discussed with reference to FIGS. 13A-13B, to close and heat a PFO.

A set of two or more such substantially axial electrodes can be splayed through a PFO tunnel to distribute energy laterally in the tunnel, while electrode pairs which extend along the length of the tunnel can serve to distribute energy through the length of the tunnel. Alternatively, non-axial shapes and patterns of electrode pairs can be deployed, such as loops, or other shapes can be used.

Figure 9C:
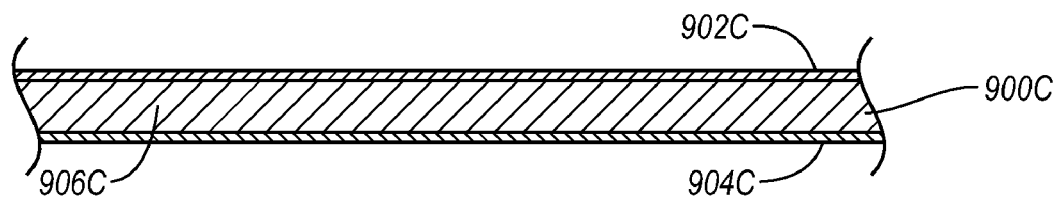

FIG. 9C is a cross-sectional view of an alternative embodiment of the an electrode 900c of present invention in which a first electrode 902c and second electrode 904c are separated one from another and positioned along the length and on opposite sides of an insulator 906c. In this embodiment, electrodes 902c, 904c can be substantially flat. In this manner, electrodes 902c, 904c can deliver energy in substantially opposite directions into tissues on opposite sides of the interior of the PFO. This energy can travel through tissues adjacent to the PFO, and travel around the device due to insulator 906c through a longer path to the other electrode. This may encourage heating of surrounding tissues due to the fact that the shortest available path is relatively circuitous. Optionally, one or more insulators can be positioned along the length of element 900c separating first electrode 902c from second electrode 904c.

Figure 9D:
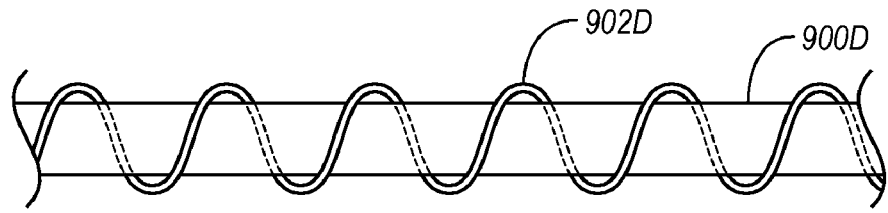

FIG. 9D illustrates an element 900d, such as an electrode, anchor, arm or delivery shaft, surrounded by a second electrode 902d wrapped around element 900d. When element 900d is an electrode, element 900d and second electrode 902d can be operated in bi-polar mode or unipolar mode. Element 900d and second electrode 900d can be electrically common elements and function together in unipolar mode with a ground, or can be electrically uncommon electrodes functioning in bipolar mode, or some combination thereof. Element 900d and second electrode 902d can be configured to concentrate energy in the interior or towards the center of element 900d. When element 900d is positioned in the PFO tunnel, the heating can be concentrated in the area immediately surrounding the tunnel area.

The illustrated electrodes of FIG. 9A-9D are generally axially configured. In the case of electrodes with radial projecting arms, which arm can engage or otherwise contact the surfaces of the septum, the concentration of energy can be highest near the center of the electrode and can decrease radially from the electrode's central axis. This can be due to the greater spread of the arms covering a larger volume of tissue between electrodes per unit tissue contact length. Thus, the current density can decline with distance from the central axis of the electrodes. In the case of plate-like electrodes with substantially uniform contact over a larger total area of the electrode, the energy delivered can be more uniform between the electrode plates and decrease radially from their outside diameter. Either of these approaches can be advantageous depending on factors such as PFO anatomy, algorithms used to deliver energy, means used to measure temperature, etc.

In some applications, because of the shape of the PFO and the positioning of the right and left electrodes against the atrial walls, the electrodes may focus applied energy differently into the primum and secundum. Accordingly, it can be advantageous to have electrode configurations that deliver energy differently to the anatomy of interest. In this manner, electrode configurations can enable adaptation of the treatment of individual PFO's to their individual characteristics.

Figure 10A:
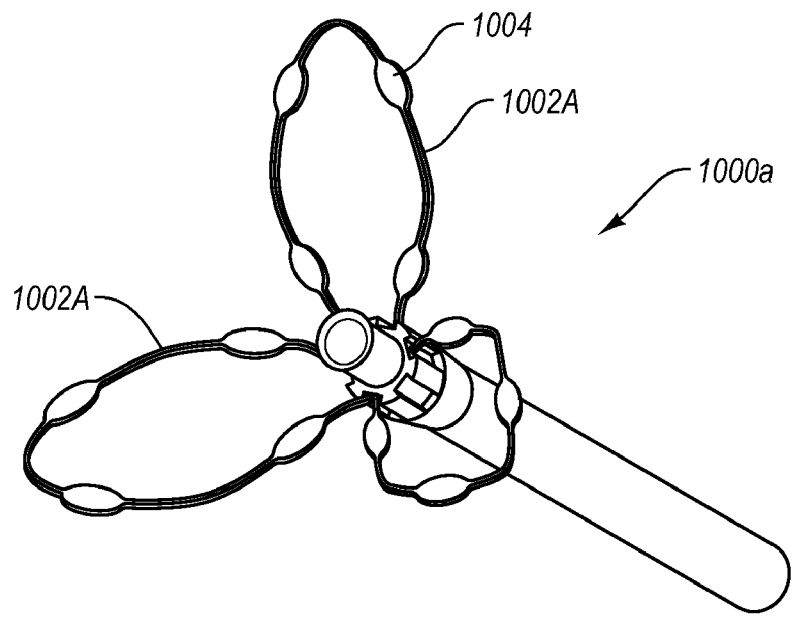
FIGS. 10A-10B illustrate schematic representations of embodiments of lobed atrial anchors of a medical device of the present invention.
Figure 10B:
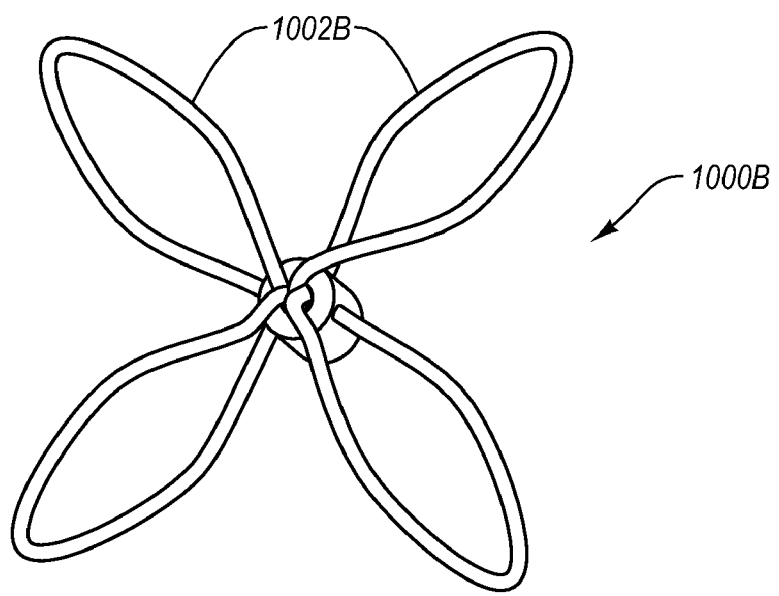

FIGS. 10A-10B illustrate embodiments of the present invention that can accommodate delivery of energy differently based upon the anatomy of interest. In FIG. 10A, a first electrode 1000a is illustrated having a plurality of arms or lobes 1002a, each arm or lobe 1002a including a contact portion 1004a having a surface area greater than the remainder of the arm or lobe 1002a. This contact portion 1004a can direct RF energy preferentially to the tissue contacting the contact portion 1004a and the tissue surrounding the contact portion 1004a. This provides enhanced control to RF energy delivery than is currently possible. The first electrode 1000a can be used in any of the configurations of closure device described herein, whether left or right anchor or electrode. As such, the discussion of first electrode 1000a is also applicable to other electrodes described herein, and vice versa.

In the illustrated embodiment, and with reference to FIGS. 10A and 1A, a three lobe 1002a design for a right anchor 1000a is illustrated, which can provide an advantageous distribution of electrical energy used to heat and close a PFO, such as PFO 50. For example, if two of the arms or lobes 1002a are positioned on the septum primum 52 (farther from the PFO tunnel 58), and the third arm 1002a is positioned on the septum secundum 54 (closer to the PFO tunnel 58), the two lobes on lower surface can inject more energy at a farther distance from the PFO 50, thus providing more heating of the tissue surrounding the PFO 50. Similarly, a three lobed left anchor can provide similar benefits. The three lobe design illustrated in FIG. 10A can also match the geometry of the entrance to the PFO 50, and thus can be advantageous in aiding repeatable positioning. One way to modify energy delivery to the tissue is by electrically connecting one or more lobes so as to serve as electrodes, while leaving other lobes electrically insulated. In this manner, RF energy can be delivered to the tissue by one or more of the clamping lobes, while the electrically insulated lobe(s) serve to position the device or to approximate tissue without RF energy delivery.

In FIG. 10B, and with reference to FIGS. 10B and 1A, a second electrode 1000*b* is illustrated having a plurality of arms or lobes 1002*b*. In the illustrated embodiment, second electrode 1000*b* includes four lobes 1002*b*. The four lobe design can deliver energy more evenly to both the septum primum 52 and septum secundum 54. In this manner, tissue immediately over the tunnel 58 may be heated relatively more than the tissues of the septum primum 54, which are farther away from the tunnel 58.

Figure 1B:
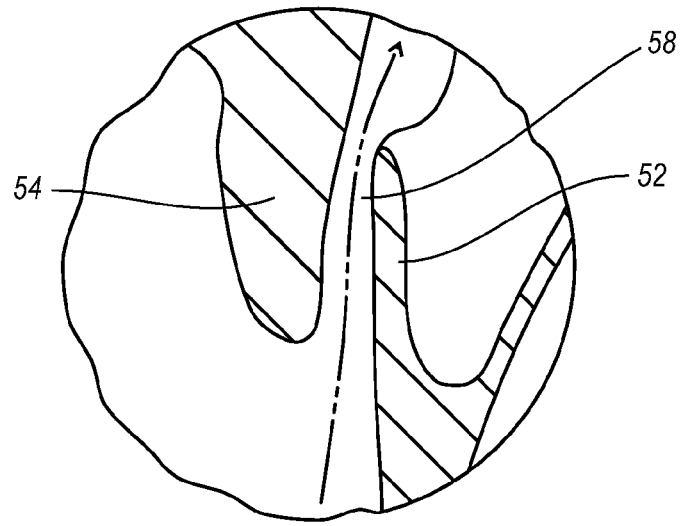
Figure 1C:
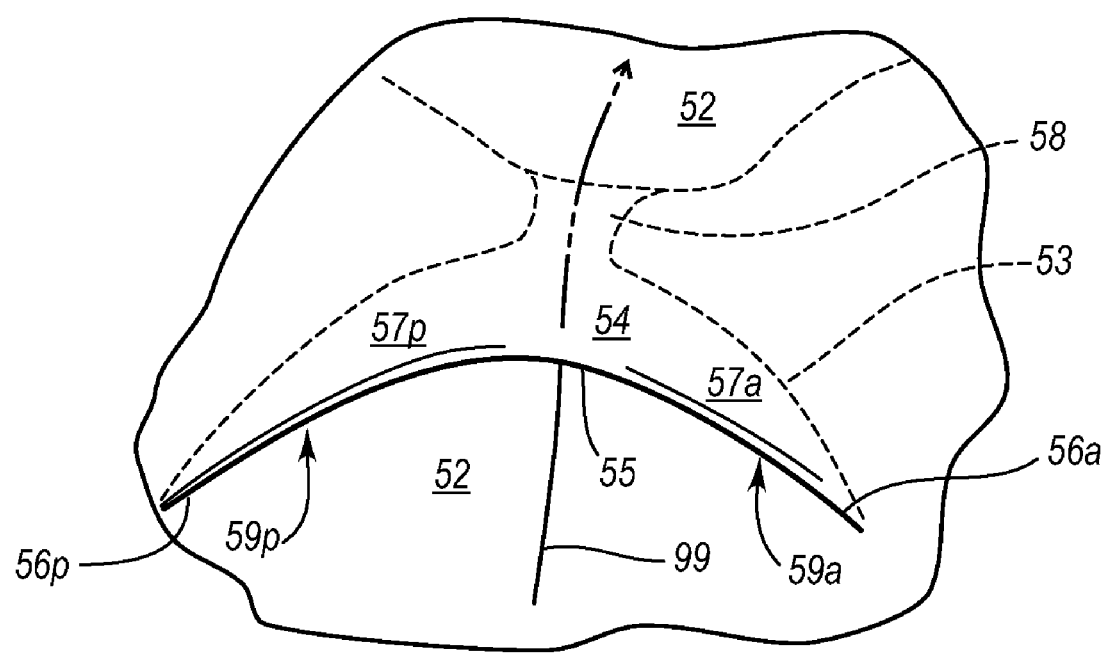

In summary, the lobed electrodes 1000*a* and 1000*b* can be configured to substantially conform to the anatomy of the wall of the right atrium 30 (FIG. 1B). Two of the lobes or arms of the anchor can tuck under the overhanging portion or arch formed by the inferior aspect 55 (FIG. 1C) of the septum secundum 54, while the third lobe can span up over the septum secundum 54. The third lobe or arm can provide clamping force and electrical contact in a desirable location to weld the PFO closed.

Figure 11A:
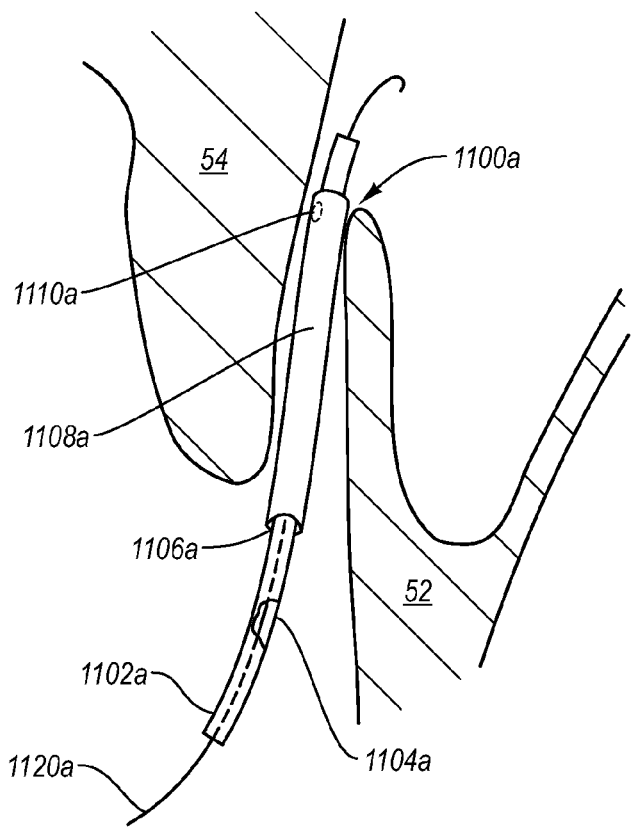
FIGS. 11A-11B illustrate a schematic representation of balloon-type medial devices of the present invention.
Figure 11B:
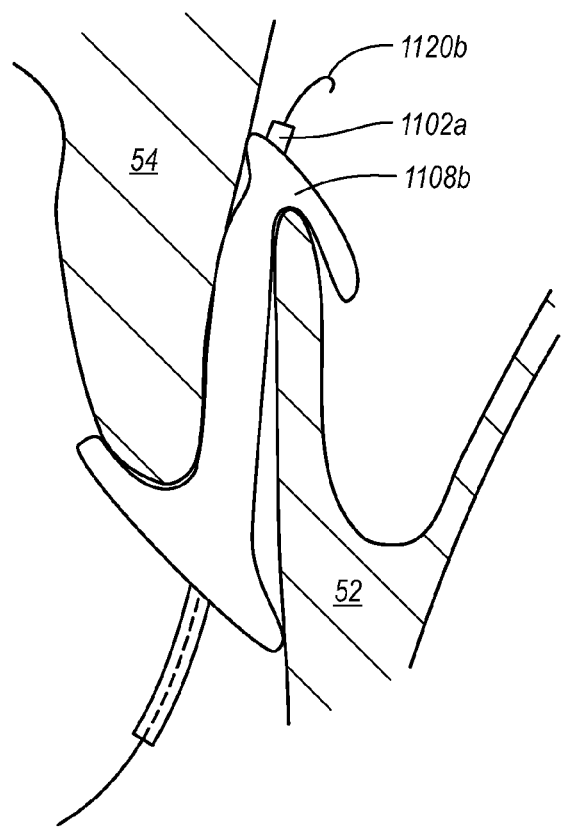

Turning to FIGS. 11A and 11B, illustrated are another electrode configuration and heating method. In this configuration, closure of the PFO 50 can be achieved through use of an elastomeric or polymeric balloon that is filled with saline or other fluid and then heated to initiate tissue damage and hence closure of the PFO 50 following removal of the balloon. With reference firstly to FIG. 11A, the balloon catheter 1100*a* includes an inflation catheter 1102*a* having a lumen 1104*a* to receive a guidewire 1120*a* and an inflation lumen 1106*a* in fluid communication with a balloon 1108*a*. Balloon catheter 1100*a* can be manufactured in a configuration that, when "inflated" with the fluid, assumes a desired shape in relation to the anatomy of the PFO 50, such as illustrated in FIG. 1B. Balloon catheter 1100*a* can be configured to be compliant and substantially conform to the anatomy of the septum, PFO, etc. Once balloon catheter 1100*a* is in position as illustrated, the liquid can be heated by means of a heater at or inside the balloon catheter 1100*a*. The fluid can be heated using electrical resistance, RF energy, optical energy, or other means, whether such heat is directed to the fluid source at the proximal end of balloon catheter 1100*a* or at the fluid within the balloon 1108*a* through heating of a heating element 1110*a* within the balloon 1108*a* as current is delivered to the heating element 1110*a*. Another means would be to introduce electrical energy through electrodes on the balloon's surface. Another would be to conduct electrical energy through the saline (or other conductive fluid) itself. Thus, the resistance of this conductive fluid would cause self-heating in response to the energy flow. In any of these heating methods, the temperature can be controlled as desired.

Balloon 1108*a*, and so balloon catheter 1100*a*, can be configured as a single device or double device, as illustrated in FIG. 11B as balloon catheter 1100*b*, on one or both ends of a PFO. It could also be small enough to reside inside the PFO tunnel when heated so as to directly heat the interior of the PFO tunnel.

The wall thickness of balloon 1108*a* or 1108*b* can be varied in desired locations to change the heating parameters of tissue adjacent balloon 1108*a* or 1108*b*. For example, the wall thickness of a portion of balloon 1108*a* or 1108*b* can be relatively thin so as to maximize heat transfer to the tissue adjacent the reduced wall portion. In other areas where balloon 1108*a* or 1108*b* is, for example, in contact with blood in the atrium, balloon 1108*a* or 1108*b* can have a thicker wall so as to reduce heat transfer to the blood or other tissues where heating is not desired.

Figure 12:
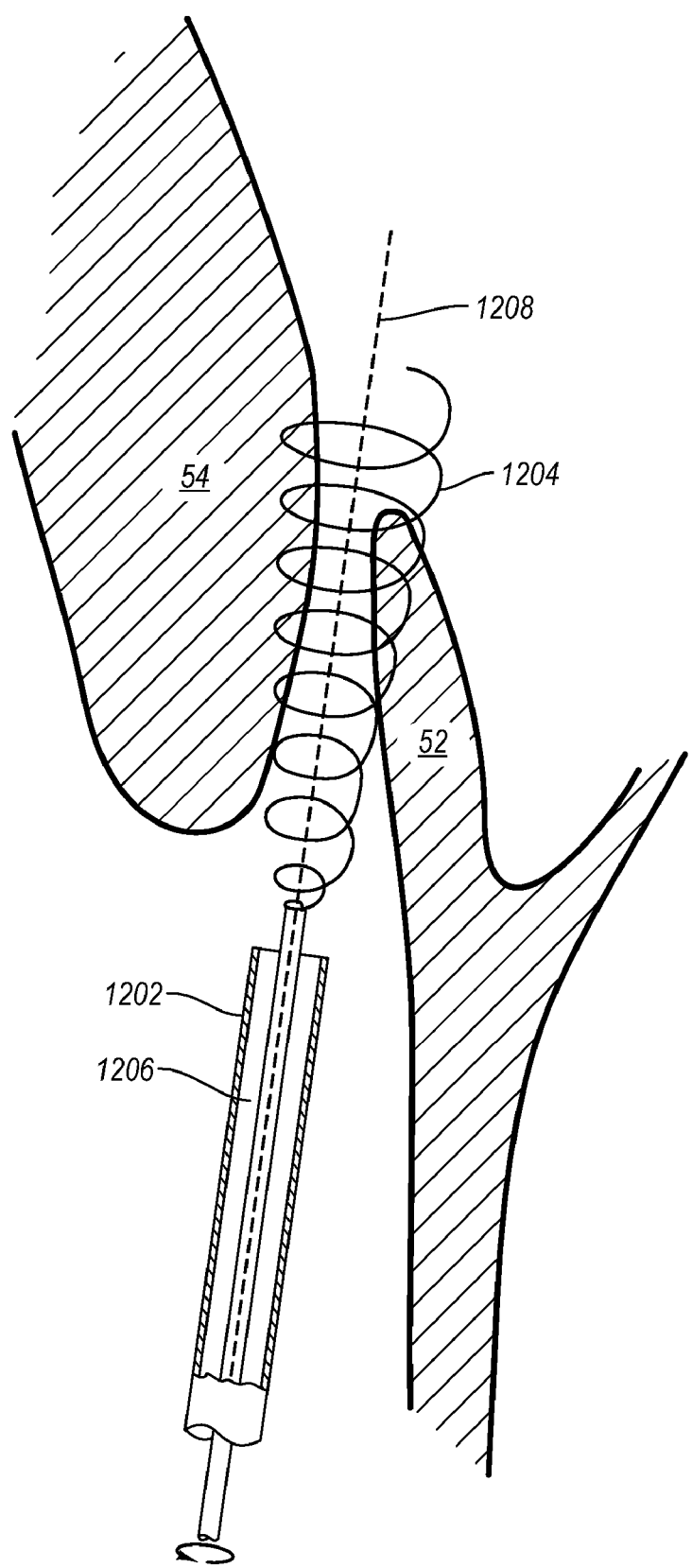
FIG. 12 illustrates a schematic representation of another embodiment of a medial device of the present invention.

Turning now to FIG. 12, illustrated is another configuration of an electrode usable to close a PFO, whether through application of RF energy, physical anchoring and closure of the PFO, or a combination of physical anchoring, whether permanently or temporarily, and application of RF energy. As illustrated, the closure device 1200 can include a delivery sheath 1202 with an anchor 1204 disposed within a lumen 1206 thereof. The anchor 1204 has a generally helical or corkscrew configuration where rotational movement of the anchor 1204 following deployment from within lumen 1206 facilitates engagement of tissue within and/or surrounding the PFO 50. The anchor 1204 can (i) function to reduce the size of the PFO 50, (ii) work as an electrode, and/or (iii) simply as a means of approximating tissues so another electrical or non-electrical means or device may be used to accomplish long-term closure.

Optionally, the anchor 1204 can include a central stem or portion 1208, illustrated in dotted lines, which can serve as a means to guide the path of the helical or corkscrew portion of anchor 1204 as it is turned into the tissue of the PFO 50. Optionally, the central stem can form a second electrode so that the anchor 1204 can operate in bipolar mode to deliver RF energy to the PFO 50. With this configuration, the heat associated with RF energy delivery will be concentrated in the area immediately surrounding the tunnel 58 (FIG. 1A) when the anchor 1204 is disposed within the PFO 50. Alternatively, the central stem 1208 and the helical or corkscrew portion of the anchor 1204 can individually operate in unipolar mode, with a separate grounding pad or return electrode (not shown) associated with patient.

The anchor 1204 can also be used to close a PFO (or other anatomical feature) when used as an implantable device that would remain in the patient after installed. The anchor 1204 can be made of material that would persist in the patient, or from biodegradable materials that could disappear after the PFO had grown closed. It can also be made of a material that would be implanted for a time, and then removed.

The anchor 1204 or other corkscrew or helical device could be made by several means. Some examples are to put a spiral slit in the end of a tube, or to wind a wire (NiTiNol, stainless steel, titanium, plastic, or other material could be used) into the desired shape. In the case of NiTiNol wire it could be formed into the desired shape and "heat set" into that shape. It could then be delivered through a small diameter tube or catheter, deployed in the atrium to its helical shape, and then "screwed" into the PFO for use. For retrieval, it could be "unscrewed" from the PFO and than pulled back into its delivery tube for removal from the patient.

As mentioned above, the particular configuration of the anchor 1204 can aid with drawing the septum secundum 54 (FIG. 1A) and septum primum 52 together. For instance, the anchor 1204 can be compliant and include a number of turns, with the first turn having a larger diameter, or being larger than thy following turns. In this embodiment, the distal tip of the anchor 1204 can be configured to penetrate and capture tissue, for example, at a certain diameter, such as in a PFO tunnel 58 (FIG. 1A). When the following smaller turns, or alternatively, closer spaced turns, are advanced into the tissue, the compliant nature of the anchor 1204 can allow the succeeding turns to expand to follow the path created by the first larger turn. Due to the configuration of the anchor 1204, the smaller succeeding turns can attempt to spring back to their smaller diameter, or in the alternative embodiment, to the closer spacing. This springing back can force the tissue surrounding the PFO 50 (FIG. 1A) together, thus closing the PFO tunnel 58 (FIG. 1A). Any desired means can then be brought to bear to "weld" the PFO closed, such as application of RF energy through the anchor 1204 and/or the central stem 1028. The anchor 1204 can then be unscrewed from the PFO with minimal disruption. Alternatively, the anchor 1204 can be biodegradable, whether or not capable of delivering RF energy to the PFO or the tunnel. In such a case, the anchor 1204 can remain within the patient until the PFO has closed.

The above-described anchor 1204 provides one structure that can be used to pull tissue together. In addition to "screwing" the anchor 1204 into the PFO tunnel 58 as described above, pulling or pushing the ends of the anchor 1204 through use of an actuating shaft mounted to either a proximal or distal end of the anchor 1204, similar to actuating shaft 118 (FIG. 2A) can aid to reduce the size of and close the PFO 50 (FIG. 1A). For instance, once in place, the ends of the anchor 1204 can be either pushed or pulled. Pushing the ends together can compress the anchor 1204 thereby capturing the tissue. Constant tissue volume can cause the tissue to squeeze into the middle, thus closing the PFO. Pulling the ends of the anchor 1204 can lengthen the anchor 1204 thereby reducing the diameter of anchor 1204. A reduced diameter can squeeze tissue towards the open PFO tunnel, thus closing it.

The pushing or pulling of the anchor 1204 can be achieved, as suggested above, by way of an actuating shaft similar to actuating shaft 118 (FIG. 2A). Alternatively, the anchor 1204 can be formed from a shape memory material, such as NiTiNol or shape memory plastics, to move the anchor 1204 from an open installation position to a closed, PFO closing, position. Optionally, the heat generated to activate the shape memory behavior of a material can also heat the surrounding tissues of the PFO, i.e., application of RF energy to the anchor 1204. Alternatively, the tissue may be heated by other means, and that heat can serve to activate the shape memory behavior. On completion of the heating step, the anchor 1204 cools and becomes pliant and can be removed.

The material forming the anchor 1204, or other medical device that can benefit from the functionality described herein, may be heated by any means that will change the temperature of the material to the appropriate level including: (i) passing electrical current through a conductive shape memory material, (ii) passing temperature-controlled fluid through tubes of shape memory material, (iii) optical, ultrasonic, electromagnetic, RF, or other energy means, or (iv) directed microwaves. Microwaves could also be used to heat PFO tissues themselves, combined with, or instead of, heating a PFO closure or heating device.

In addition to the anchor configuration described above, alternative configurations of medical devices or anchors/electrodes can be utilized to close a PFO by pushing and/or pulling. For example, intertwined or overlapping helices or corkscrews devices similar to anchor 1204 can be utilized. These can be installed around the PFO tunnel, similar to as described above with regards to the corkscrew configuration. Pulling apart causes the approximately tubular shape to decrease in diameter and grip the PFO more tightly. Pushing can also have a beneficial compressive effect. In a different configuration, straight elements can be utilized, which elements can penetrate the tissue surrounding the PFO. The ends of the elements are then captured and pulled together, thus pulling the PFO together. In yet another configuration, two elements configured with substantially straight portions and curved portions can be utilized. The elements can be inserted into the tissue surrounding the PFO and then come together at each end. The elements can be configured such that as the ends of the elements are pulled together, the center sections of elements are forced together.

As with the anchor 1204, closing the above-described devices can be achieved through physically pulling or pushing ends apart or together or through using of the superelastic and/or shape memory characteristics of the material forming the device.

Figure 13A:
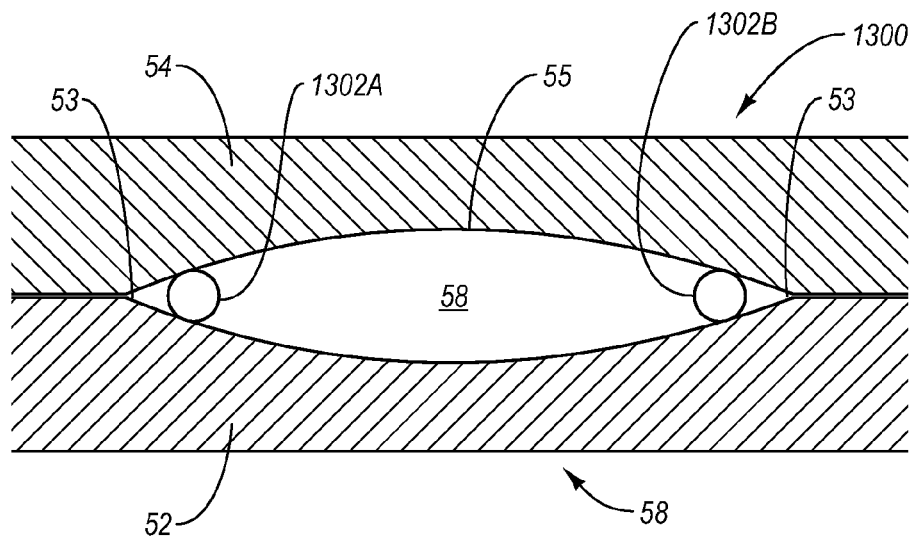
FIGS. 13A-B illustrate a schematic representation of one embodiment of a medial device of the present invention.
Figure 13B:
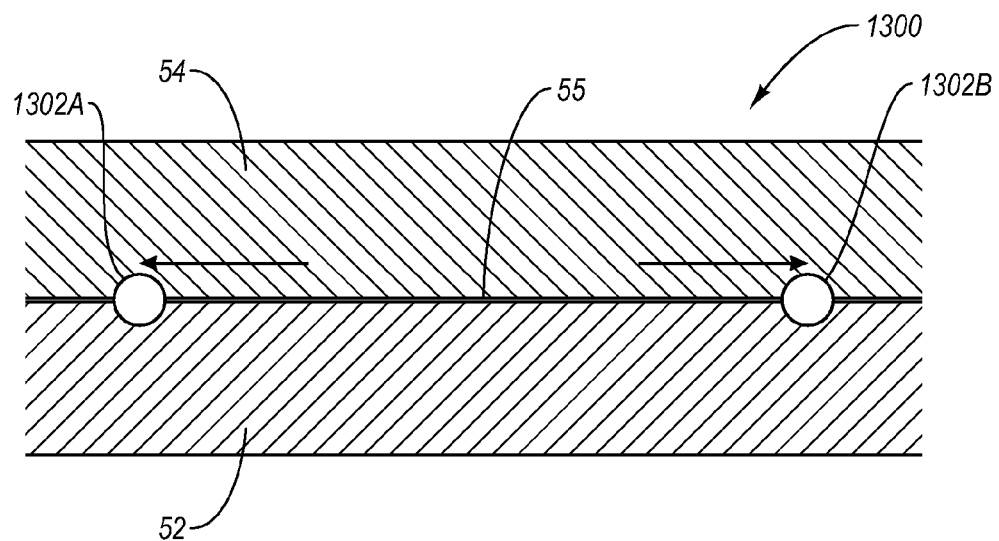

Turning to FIGS. 13A-13B, illustrated is another device capable of being used to close a PFO. The anatomy of a PFO is such that its tunnel 58 (FIG. 1A) is somewhat of a flattened opening formed between two tissue flaps, i.e., the septum primum 52 (FIG. 1A) and septum secundum 54 (FIG. 1A). A PFO closure device 1300 may be formed from two substantially parallel rods that may be placed through the tunnel 58, as illustrated in FIGS. 13A-13B. In FIG. 13A, the medical device 1300 is illustrated as having two rods 1302*a,b* positioned in the tunnel 58 of the PFO 50. If these rods 1302*a,b* are spread apart in the plane of the tunnel 58, as illustrated in FIG. 13B, they will stretch the edges of the tunnel 58 apart, thus bringing the two more planar tunnel surfaces together. The rods 1302*a,b* can be straight or curved to maintain an approximately even spreading force along the length of the PFO tunnel 58. The rods 1302*a,b* can be configured to include curved sections or other shapes can be used to concentrate spreading forces in desired locations of the PFO 50.

Rods 1302*a,b* can be formed from tubular structures, solid structures, combinations thereof, or other structures that can be used to move one a lateral direction to move portions of the tunnel 58 towards each other. In this embodiment, the closure effect could be enhanced by providing ports through which a vacuum may be pulled. This vacuum would tend to pull the surfaces of the PFO even closure together. Additionally, one rod could deliver heated fluid such as saline, while the other rod can provide a vacuum at its ports. If the pressure delivery and vacuum were balanced the vacuum would still predominate so that it could continue to pull the PFO closed while keeping the heated fluid localized to the interior of the PFO. The heated fluid can heat the tissues of the PFO tunnel. Alternatively, the rods 1302*a,b* can include electrodes in an RF energy delivery system. In this embodiment, rods 1302*a,b* can be used to heat the interior of the tunnel. In this manner, the energy delivery can be distributed evenly along the length of the tunnel, and nearest the interior surfaces of the tunnel.

Returning to FIG. 2A, as mentioned above, the left atrial anchor or electrode 114 can be formed with the delivery shaft 110. This can be achieved using a slit-tube configuration as disclosed in U.S. patent application Ser. No. 11/671,428, filed Feb. 5, 2007. With the configuration, the arms 116 can be used to close the PFO 50. The arms 116 can be configured to be either in a normally-closed or normally-extended configuration. In a normally-closed configuration, the actuating shaft 118 is moved proximally to "pull" the arms 116 into the desired configuration. Releasing the actuating shaft 118 returns the anchor/electrode to the low-profile configuration. In contrast, for a normally extended configuration, the actuating shaft 118 is moved distally to move the arms 116 into the low-profile configuration used to initially position and remove the anchor/electrode. In the former, the anchor/electrode can be removed even if the actuating shaft 118 should fail or become disconnected.

Another embodiment of a medical device which is configured to be used in connection with physically closing a PFO includes electrodes or clamps with hinges or pivots. Another desirable feature of electrodes can include a feature that enables the electrode/clamp to pivot. Pivoting enables the electrode or clamp to become planar on the septum while a center stem passes through a PFO that is sharply angled to the septum. Various configurations can accomplish this hinging effect. For example, in one embodiment hinged clamps can be used. The electrode or clamp device can move into contact with the PFO, the primum, and the secundum, in such a way as to not distort the tissues inappropriately.

An electrode or clamping device can be formed which incorporates the use of hinges or pivots in place of flexures. One way to form such a pivot is to connect two relatively rigid elements with a flexible element. One way to accomplish this is to place a flexible element, such as, but not limited to, a string-like thread or wire through the bore of sections of tube. It may then be knotted or attached so as to prevent the flexible element from being pulled out of the tube(s) when tension is applied to the flexible element. Alternatively, such a flexible element may be used to tie the ends of two rigid elements together. This flexible element may be formed from wire (e.g. nitinol, stranded wire, etc.), or from items such as fishing line, dental floss, thread or string as one might find commercially. This flexible element can be made from polymers such as nylon, linearized polyethylene, Spectra, aramid, polyamide, Kevlar, Nomex, or other materials.

At the joint between tube segments, the segments can be free to move with little restriction if the flexible element is left loose. This creates a true hinge or pivot. The segments can be partially constrained by applying some tension to the flexible element. This can cause the two adjacent ends of the tube to remain next to each other, thus providing some constraint while still allowing for relative pivoting. Pivoting can be enhanced by providing spherical ends on one or both adjacent bead or tube ends. Examples of various hinging embodiments are set forth in FIGS. 14A-14F.

FIG. 14A discloses a medical device 1400A that can include a flexible element 1402, such as a securing wire and a plurality of round members 1404 linked together by flexible element 1402. Round members 1404 can include a channel through which flexible element 1402 can be received to link round members 1404 together. In this manner, flexible element 1402 can move within round members 1404. As flexible element 1402 is tightened and round members 1404 are forced together, the configuration of round members 1404 will enable round members 1404 to effectively function as a hinge.

Likewise, FIG. 14B discloses a medical device 1400B that can include a flexible element 1402 and a plurality of elements 1406 linked together by flexible element 1402. Elements 1406 can include an aperture through which flexible element 1402 can be received to link elements 1406 together. In this manner, flexible element 1402 can move through and with respect to elements 1406. As flexible element 1402 is tightened and elements 1406 are forced together, elements 1406 can move relative to each other and are otherwise hingedly linked together.

FIG. 14C discloses a medical device 1400C that can include a flexible element 1402 and a plurality of elements 1406 linked together by individual flexible element 1402. Elements 1406 can include an aperture through which flexible element 1402 can be received to link elements 1406 together. In this manner, flexible element 1402 can function as a hinge as elements 1406 can move relative to each other.

FIG. 14D discloses a medical device 1400D that can include a flexible element 1402 and a plurality of tubular elements 1408 linked together by flexible element 1402. Tubular elements 1408 can be configured such that flexible element 1402 can be received therethrough to link tubular elements 1408 together. Medical device 1400D can include a stop 1410 coupled to flexible element 1402 to facilitate forcing tubular elements 1408 together as tension is applied to flexible element 1402. In this manner, flexible element 1402 can move through and with respect to tubular elements 1408, but can be prevented from pulling through tubular elements 1408 due to stop 1410. As flexible element 1402 is tightened and tubular elements 1408 are forced together, as illustrated in FIG. 14E, tubular elements 1408 can move relative to each other and are otherwise hingedly linked together at adjacent ends.

To enable a smoother hinging interaction between tubular elements 1408, alternative tubular elements 1412a, b can be utilized, as illustrated in FIG. 14F with regards to medical device 1400F. In this embodiment, tubular elements 1412a,b can include ends having corresponding shapes. Corresponding shapes of adjacent ends of tubular elements 1412a,b can increase the hinging flexibility of tubular elements 1412a,b when flexible element 1402 is pulled taut, as illustrated in FIG. 14F. Similarly, the substantially round members 1404 of FIG. 14A can also be provided with corresponding shapes on their contacting surfaces to enable a smooth interaction between members 1404.

Figure 15A:
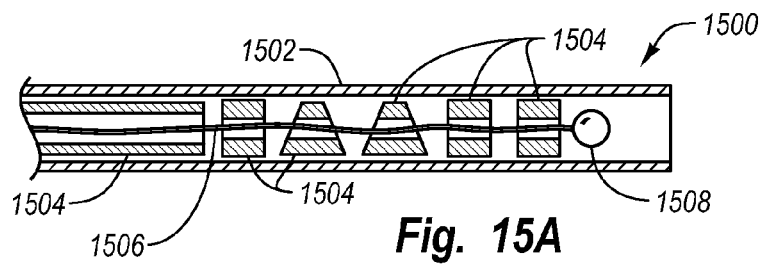
FIGS. 15A-C illustrate a schematic representation of one embodiment of a medial device of the present invention.
Figure 15B:
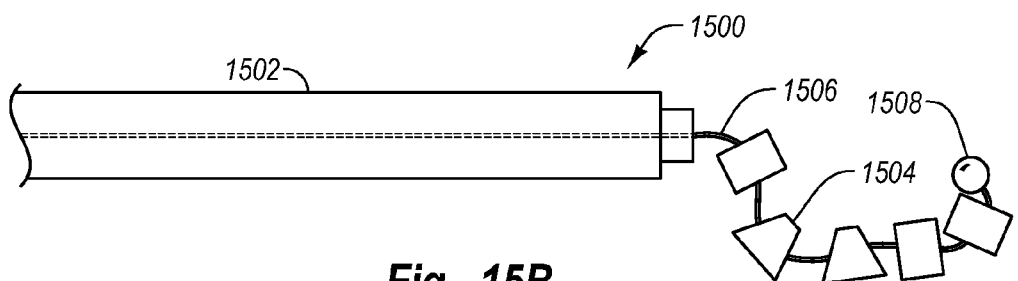
Figure 15C:
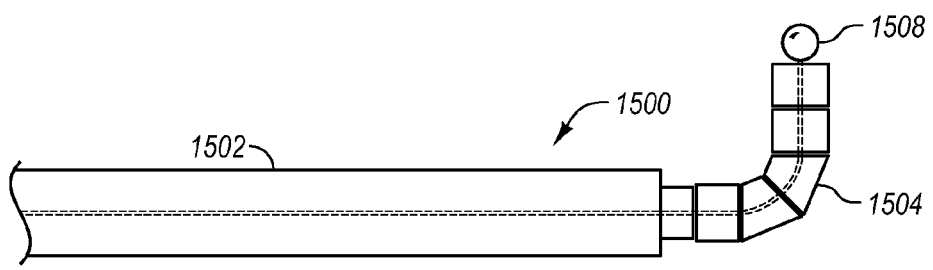

FIGS. 15A-15C illustrate an embodiment of a medical device 1500 having self-erecting/self-configuring shaped segments 1504 that may be delivered through a tube 1502. Segments 1504 can be sized and configured to form a desired shape when a flexible element 1506, such as a securing wire, which is strung through segments 1504, is tensioned. For example, segments 1504 can include angled, straight or rounded edges, or can include a combination of shapes in order to form a desired shape when flexible element 1506 is tensioned. Various features of segments 1504 can optionally be included that maintain the rotational orientation of one shape segment 1504 relative to another (e.g. particular end shapes, mechanical keys, a second string through a second lumen, etc.).

After segments 1504 are pushed out of tube 1502, as illustrated in FIG. 15B, flexible element 1506 can be pulled. Pulling flexible element 1506 can cause stop 1508 to contact and engage the adjacent segment 1504, thereby resulting in the other segments 1504 to come together to form or assume the desired shape, as illustrated in FIG. 15C. By forming segments 1504 with angles and various shapes, as well as in various patterns, orientations, and sequences, specific two and three dimensional shapes can be formed when flexible element 1506 is pulled. Such a self-erecting string of beads, tubes or segments could be fed through a tube. When the beads, tubes or segments are out of the tube, the flexible element could be pulled, and the beads/segments prevented from re-entering the tube by a "pusher." This would cause the structure to self-erect.

Figure 16:
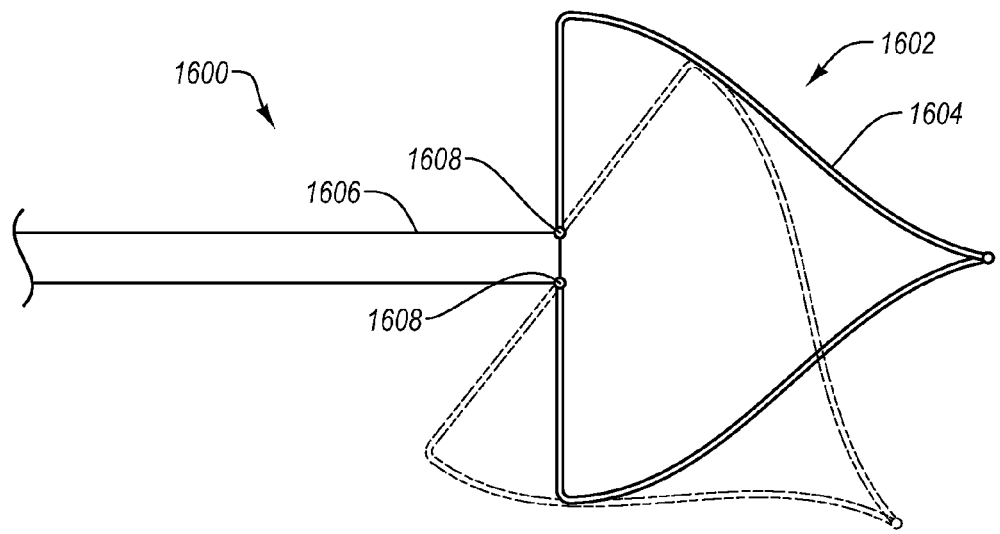
FIG. 16 illustrates a schematic representation of one embodiment of a medial device of the present invention.

Various electrodes and clamps can benefit from utilizing the configurations of those devices illustrated in FIGS. 14A-15C, such devices including one or more hinges or joints as described herein. The electrodes disclosed herein and the references incorporated by reference can benefit from the use of a pivot. It can be desirable to control the free ends of a free end electrode by some means to prevent anatomical tangling. This means can constrain the wires or arms in a way that allows the arms to be retracted into a delivery tube after use. One means of accomplishing this is to constrain these free ends by connecting them with a pivot that will prevent the wires or arms from moving through undesired motions, yet allow the wires or arms to move through desirable ones. One example of this is illustrated in FIG. 16. FIG. 16 illustrates a medical device 1600 that can include an electrode or left atrial anchor 1602 having arms 1604 hingedly coupled to a stem or shaft 1606 by pivots or hinges 1608. As illustrated by the dotted lines in FIG. 16, as electrode/anchor 1602 is deflected, pivots or hinges 1608 enable electrode/anchor 1602 to rotate relative to stem 1606.

In order to obtain the desired performance, the tips of the arms 1604 or wires can include a pivot or hinge 1608 of some kind that will partially constrain the ends of the arms 1604 or wires, yet allow appropriate deployment and shape. These hinges or pivots 1608 may be accomplished, for example, by bending the tips of the wires around each other to form a pivot, replacing the wires with tubes with an internal string, or other methods such as ball and socket or other designs.

Figure 17:
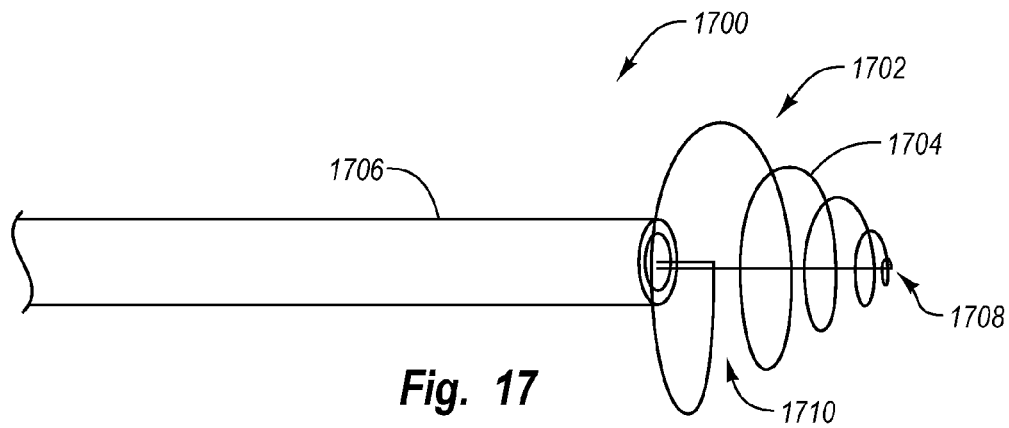
FIG. 17 illustrates a schematic representation of one embodiment of a medial device of the present invention.

FIG. 17 illustrates yet another medical device 1700 in accordance with an alternative embodiment of the present invention. Medical device 1700 can include an anchor or electrode 1702 extending from a stem or shaft 1706. Electrode 1702 can form a coil from a single (Nitinol or other flexible) wire 1704 in which the distal end 1708 of the wire 1704 forms the smallest coil or loop and the proximal end 1710 forms the largest coil or loop, as illustrated in FIG. 17. Electrode 1702 can be configured to be received and substantially housed by shaft 1706, and can be extended therefrom to form electrode 1702 as illustrated.

In this embodiment, when electrode 1702 is housed in tube 1706 and as the distal end 1708 of the wire 1704 exits the delivery tube 1706, a very small coil or loop forms initially, which has little probability of encountering anatomical structures. As more wire 1704 is deployed behind the first coil, the electrode 1702 can assume the coiled shape in an orderly and controlled manner. A portion of the wire 1704 will rotate in a relatively smaller diameter at the center of a growing spiral. As such it can be protected and prevented from encountering anatomical structures as it is deployed. The electrode 1702 can be configured to form in a plane perpendicular to its delivery tube 1706. Alternatively, the electrode 1702 can be formed to deploy such that the coil's axis is perpendicular to the axis of the delivery tube 1706. In this case, the last wire to be pushed from the delivery tube 1706 may be configured to cause the coil to rotate over to a substantially perpendicular position.

In an alternative embodiment, the electrode can have a free end having a small diameter coil at its distal end, which as electrode is pushed or turned out of the delivery tube, the diameter of the coils increase. In this embodiment, the electrode extends axially in the distal direction, such that the largest diameter coil is adjacent the distal end of the delivery tube and the smallest diameter coil is positioned axially away from the distal end of the delivery tube in the distal direction. Alternatively, the electrode can be configured to coil around the delivery tube, such that the smallest diameter coil is positioned in the proximal direction from the distal end of the delivery tube, with the diameter of the coils increasing up to the distal end of the delivery tube.

It will be appreciated by one of ordinary skill in the art in view of the disclosure proved herein that electrodes of the present invention can be formed with a single or multiple coils. For example, a double coil, conical spring electrode/anchor can be formed. The first wire to exit the delivery tube forms an initial small diameter coil. The coil can grow to a maximum and then decrease in diameter as more wire exits the delivery tube. It finishes with a final small diameter coil that then turns into a substantially straight wire that returns into the delivery tube.

In the example of a spiral coil electrode, its stiffness and shape recovery properties can be balanced and configured as desired by varying the diameter of the coils formed while varying the diameter of the wire that forms the coil. This enables different coils having desired strengths to be provided. For instance, coils having thicker wire and a smaller coil, and vice versa, are possible. However, small diameter coils and thick wire both can cause undesirable strain levels in the wire when it is inside a delivery tube. This can be overcome by forming the wire such that it has a smaller diameter in the area where the smaller diameter coils are formed. The larger diameter coils can be formed from thicker wire because they are not required to bend as tightly. The fact that stiffness of a wire increases with the cube of the thickness, but strain increases linearly with thickness, can be used as an advantage in designing the coil.

Figure 18A:
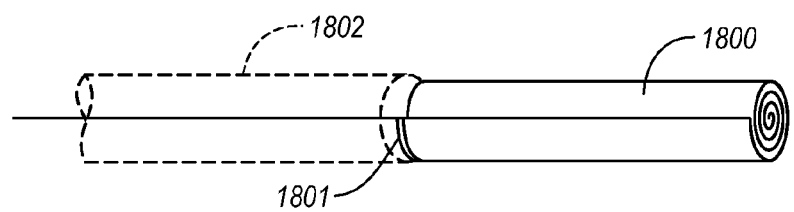
FIGS. 18A-18B illustrate a schematic representation of another embodiment of a medical device of the present invention.
Figure 18B:
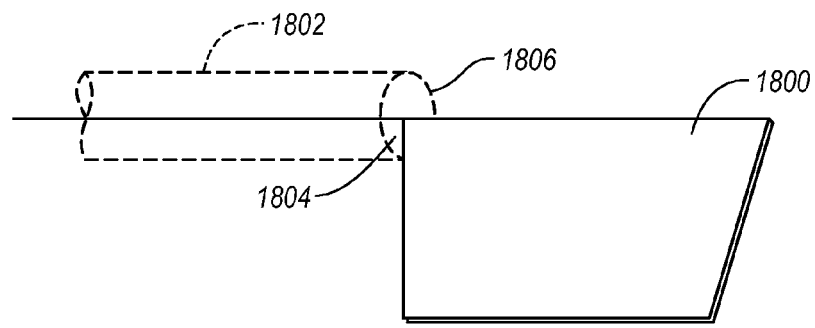

An electrode formed from a shape memory material or superelastic material, such as electrode 1800 illustrated in FIGS. 18A and 18B, can also be formed such that it will deploy from a tubular shape, as illustrated in FIG. 18A, into a partly or fully unrolled shape, optionally having a flat configuration, as illustrated in FIG. 18B. As illustrated, the electrode 1800 can include a delivery tube 1802, such as a catheter, that defines the outer periphery of the electrode 1800 while positioned in the tube 1802. The frame 1801 can support the electrode 1800 and facilitate transition to the unrolled configuration. All or a substantial portion of the electrode 1800 can be formed of a shape memory or superelastic material.

The electrode 1800 can fit advantageously into the approximately flat PFO tunnel shape, or fit flat against anatomical structures, such as the septum. Such flat, or partly unrolled, electrode 1800 can be delivered through a delivery tube 1802 and unrolled as it exits the tube 1802. The proximal end 1804 of the flattened shape can be configured so as to cause the proximal end 1804 to re-roll when it is retracted into the delivery tube 1802. For instance, the proximal end 1804 can have a tapered configuration such that engagement of the proximal end 1804 with the distal end 1806 of the delivery tube 1802 induces rotational motion of the electrode 1800. This rotational motion continues as the electrode 1800 is drawn into the delivery tube 1802.

Figure 19:
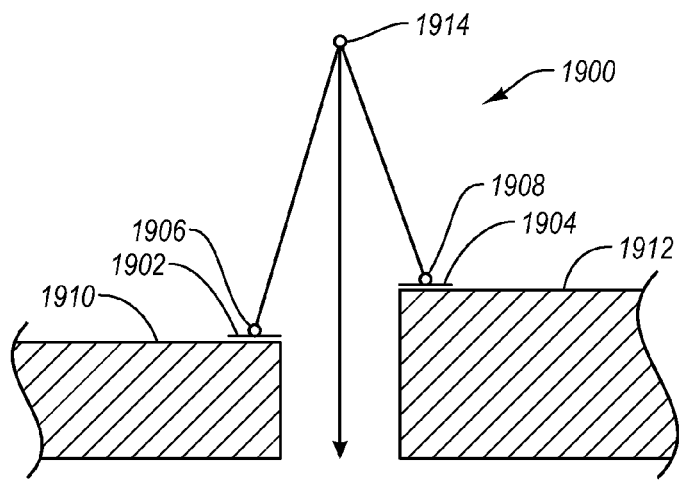
FIG. 19 illustrates a schematic representation of one embodiment of a medial device of the present invention.

According to another configuration of the present invention, an electrode/tissue tissue clamp can be configured to contact uniformly even on irregular and/or non-planar surfaces. FIG. 19 illustrates a schematic representation of such an electrode, identified as electrode 1900. In the illustrated embodiment, electrode 1900 can include one or more feet 1902, 1904 configured to contact surfaces 1910, 1912, respectively. When the electrode 1900 is pushed or pulled onto a surface, such as surfaces 1910, 1912, the electrode 1900 can pivot in such a way as to maintain contact with higher and lower areas of the surface 1910, 1912. The electrode 1900 can include one or more hinges or joints 1906, 1908, and 1914 to accomplish this leveling effect. In this manner, the loads on one leg of the electrode 1900 can be approximately equal to the load on the other. The pivots 1906, 1908, and 1914 may be formed as true pivots, flexures, or any other hinge as discussed and/or disclosed here.

In delivering devices to the heart or other anatomy, it can be desirable to configure the flexibility of the catheter used for delivery. For example, it can be desirable to achieve lateral flexibility while preserving axial and/or torsional stiffness. This can be accomplished by various tube slitting methods to achieve the desired balance of characteristics. For example, a tube may be cut in various patterns to achieve a balanced combination of flexibility & stiffness. The spacing, geometry, and number of cuts, slits or holes can be varied to achieve a desired characteristic. Torsional vs. axial stiffness can be balanced and/or varied by the angles and widths of struts left between the holes or cuts, as also varying the angle of the sides of cutouts and struts. Relative position of the holes leaves wider or narrower struts in different directions, thus affecting flexibility and other characteristics.

Figure 20A:
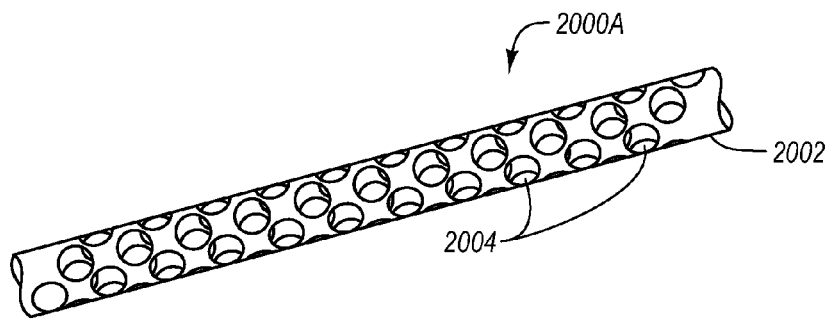
FIGS. 20A-C illustrate schematic representations of embodiments of a medical device of the present invention.
Figure 20B:
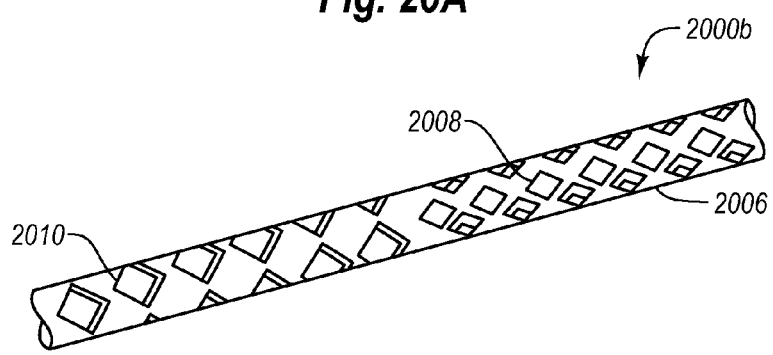
Figure 20C:
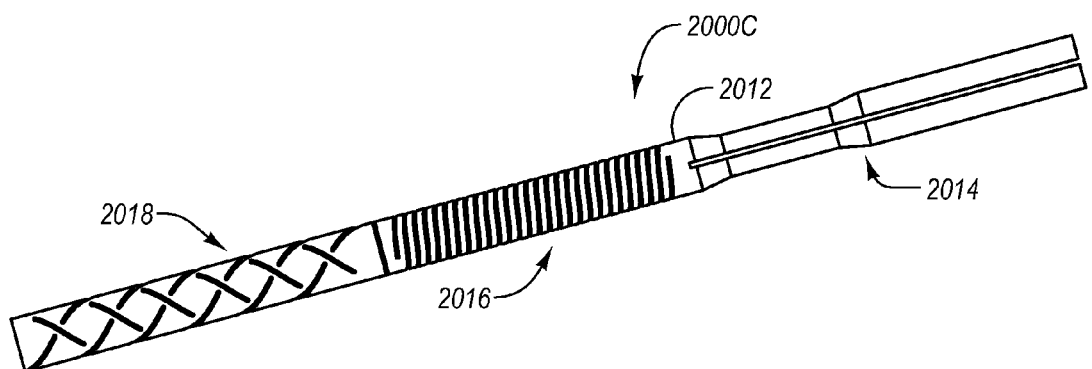

FIGS. 20A-20C illustrate examples of cut patterns. For example, FIG. 20A illustrates a catheter 2002 having a plurality of holes 2004 cut therethrough. FIG. 20B illustrates a catheter 2006 having a pattern of shapes 2008, 2010, such as diamonds, cut therethrough. As shown in the illustrated embodiment, the catheter 2006 can include uniform patterns, as with shapes 2008, can include shapes 2010 having varied position, or can include combinations thereof. Similarly, FIG. 20C illustrates a catheter 2012 having a pattern of cut shapes along its length. In the illustrated embodiment, catheter 2012 can include herringbone patterns of slits 2018, slits around the perimeter of the catheter 2016, slits parallel to the axis of the catheter 2014, portions of reduced wall thicknesses and/or reduced diameter, or staggered parallel slits, whether diagonal or axial. It will be understood by one of ordinary skill in the art in view of the disclosure provided herein that the shapes and patterns can be sized, configured and positioned to provide a desired effect.

Generally, the present invention can be embodied in a number of different configurations. One skilled in the art will appreciate that the disclosure related to one embodiment described herein can also apply to other embodiments and structures and that the functions of one device or portion of the device can be used and incorporated within other embodiments. Further, RF energy or other heating methods described herein may be used in combination with permanently or temporarily implanted devices, or by bioresorbable devices to close a body lumen, such as a PFO, or "weld" tissues together.

Generally, a medical device can include a first radio frequency conductive electrode, a second electrode spaced apart from and movable relative to said first electrode, wherein the spacing between said first electrode and said second electrode is selectively changeable to accommodate for variations in a length of a tunnel of a Patent Foramen Ovale. Each of the first and second electrodes can be conductive to radio frequency energy. The medical device can further include a means for varying the spacing between said first electrode and said second electrode. The means for varying the spacing can include a delivery shaft coupled to the first electrode. The first electrode and said second electrode can be formed as separate portions of a single compliant electrode.

In another configuration, a medical device can include a first atrial anchor, a first delivery shaft linked to said first atrial anchor, wherein said first delivery shaft is adapted to move said first atrial anchor, a second atrial anchor, a second delivery shaft linked to said second atrial anchor, wherein said second delivery shaft is adapted to move said second atrial anchor, and a biasing member linking either (i) said first atrial anchor to said first delivery shaft or (ii) said second atrial anchor to said second delivery shaft. The biasing member can include a spring, and can link said first atrial anchor to said first delivery shaft, or link said second atrial anchor to said second delivery shaft. The medical device can further include a second biasing member, wherein said first biasing member links said first atrial anchor to said first delivery shaft and said second biasing member links said second atrial anchor to said second delivery shaft.

In an alternative configuration, a medical device can include a first electrode having a stem and one or more conductive arms, wherein said one or more arms are adapted to be coupled to said stem, a second electrode having one or more conductive arms, and an insulating material coupled to at least a portion of: (i) said first electrode, or (ii) said second electrode, said insulating material adapted to reduce the conductivity of said at least a portion of said first electrode or said second electrode. The insulating material can be coupled to: (i) said first electrode, (ii) a portion of at least one of said one or more conductive arms of said first electrode, (iii) a portion of said stem, (iv) a portion of at least one of said one or more conductive arms of said first electrode and said stem, (v) a portion of said second electrode, (vi) a portion of at least one of said one or more conductive arms of said second electrode, or (vii) a portion of said first and second electrodes.

As described herein, a method for treating an internal tissue opening can include placing a medical device in position to treat an internal tissue opening, said medical device comprising a first electrode and a second electrode, wherein said first electrode and said second electrode are adapted to operate in both a unipolar mode and a bipolar mode, positioning said first electrode adjacent a first side of the internal tissue opening, positioning said second electrode adjacent a second side of the internal tissue opening, and operating said first and second electrodes between said unipolar and bipolar modes. The medical device can further include a conductive stem, wherein said conductive stem is adapted to operate in both a unipolar mode and a bipolar mode. The conductive stem can be a delivery shaft or a delivery tube, as used herein. The method can further include operating said conductive stem to heat the tissue adjacent the internal tissue opening. In this method, operating said first and second electrodes can heat the tissue adjacent the internal tissue opening. The method can further include heating the tissue adjacent the internal tissue opening by operating said first and second electrodes in unipolar mode, and operating said first and second electrodes in bipoloar mode. The method can include first and second electrodes operating in unipolar mode simultaneously or at different time, for the same or differing durations, at the same or differing power levels.

In another configuration, a medical device can include a first atrial anchor having one or more compliant arms, a shaft adapted to be coupled to said first atrial anchor, wherein movement of said shaft causes movement of said first atrial anchor, a second atrial anchor having one or more compliant arms, and a second shaft adapted to be coupled to said second atrial anchor, wherein movement of said second shaft causes movement of said second atrial anchor, wherein said second shaft is adapted to be received and movable within said first shaft. The one or more compliant arms of said first atrial anchor can be adapted to deflect when forced against tissue, and then conform back to the predeflected orientation when not forced against the tissue.

In still another configuration, a medical device can include a first atrial anchor, a first delivery shaft linked to said first atrial anchor, wherein said first delivery shaft is adapted to move said first atrial anchor, a second atrial anchor, a second delivery shaft linked to said second atrial anchor, wherein said second delivery shaft is adapted to move said second atrial anchor, and a biasing member linked to at least one of said first delivery shaft or said second delivery shaft. The biasing member can include a spring. The biasing member can link said first atrial anchor to said first delivery shaft. The medical device can further include a handle coupled to said first delivery shaft, wherein said biasing member links said first delivery shaft to said second delivery shaft, wherein said biasing member is adapted to bias the position of said first delivery shaft with respect to said second delivery shaft.

In yet another configuration, a medical device can also include a first radio frequency conductive electrode a radio frequency conductive stem adapted to be coupled to said first electrode, and a second radio frequency conductive electrode, wherein said first electrode and said second electrode are electrically common elements. The medical device can further include a radio frequency conductive stem, such as a delivery shaft.

In another configuration, a medical device can include a first atrial anchor, a delivery shaft adapted to be coupled to said first atrial anchor, wherein said delivery shaft is adapted to move said first atrial anchor, a second atrial anchor, a first electrode, and a second electrode, wherein said first and second electrodes are both coupled to at least one of said first atrial anchor, said delivery shaft or said second atrial anchor. The first and second electrodes can be wrapped around at least a portion of said at least one of said first atrial anchor, said delivery shaft or said second atrial anchor in a spiral fashion along at least a portion of the length of said at least one of said first atrial anchor, said delivery shaft or said second atrial anchor. The medical device can further include an insulator coupled to said at least one of said first atrial anchor, said delivery shaft or said second atrial anchor, wherein said insulator is positioned between said first electrode and said second electrode and is adapted to position said first electrode apart from said second electrode. An insulator can be positioned on one or more of the first atrial anchor, second atrial anchor, or the delivery shaft. Furthermore, insulator can have varying thickness, can have a constant thickness or can be a combination thereof, over a desired area of medical device.

Still another configuration of a medical device can include a medical device having a first atrial anchor, a delivery shaft adapted to be coupled to said first atrial anchor, wherein said delivery shaft is adapted to move said first atrial anchor, a second atrial anchor, and a first electrode, wherein at least one of said first atrial anchor, said delivery shaft or said second atrial anchor comprises a second electrode, wherein said first electrode is adapted to operate with said second electrode to heat tissue adjacent said first and second electrodes, wherein said first electrode is wrapped around at least a portion of said at least one of said first atrial anchor, said delivery shaft or said second atrial anchor. The first electrode can be wrapped around said at least one of said first atrial anchor, said delivery shaft or said second atrial anchor in a spiral fashion along at least a portion of the length of said at least one of said first atrial anchor, said delivery shaft or said second atrial anchor. The delivery shaft can include the second electrode, said first electrode is wrapped around at least a portion of said delivery shaft in a spiral fashion along at least a portion of the length of said delivery shaft.

Still another a medical device can include a first atrial anchor, a delivery shaft adapted to move said first atrial anchor, a hinge linking said first atrial anchor to said delivery shaft, wherein said hinge is adapted to enable first atrial anchor to move relative to said delivery shaft, and a second atrial anchor. The medical device can further include a second delivery shaft and a second hinge linking said second atrial anchor to said second delivery shaft.

The present invention may be embodied in other specific forms without departing from its spirit or essential characteristics. The described embodiments are to be considered in all respects only as illustrative and not restrictive. Exemplary claims have been included herein to illustrate embodiments of the invention. Although exemplary claims are presented, the invention is not limited to these claims, and the applicant reserves the right to present different or other claims in the future in view of the embodiments of the invention described herein.

What is claimed is:

1. A medical device comprising:
a first electrode having a stem and one or more conductive arms, the first electrode being selectively positionable from a first state within a delivery sheath to a second state wherein the first electrode is fully deployed from the delivery sheath;
a second electrode having one or more conductive arms, the second electrode being selectively positionable from a first state within the delivery sheath to a second state wherein the second electrode is fully deployed from the delivery sheath, wherein the first electrode, including the stem, and the second electrode are displaceable relative to one another while each maintains its respective second, fully deployed state;
a third electrode disposed between the first electrode and the second electrode; and
an insulating material coupled to at least a portion of: (i) the first electrode, or (ii) the second electrode.

2. The medical device of claim 1, wherein the insulating material is coupled to said first electrode.

3. The medical device of claim 1, wherein the insulating material is coupled to a portion of at least one of the one or more conductive arms of the first electrode.

4. The medical device of claim 1, wherein the insulating material is coupled to a portion of the stem.

5. The medical device of claim 1, wherein the insulating material is coupled to a portion of at least one of the one or more conductive arms of the first electrode and the stem.

6. The medical device of claim 1, wherein the insulating material is coupled to a portion of the second electrode.

7. The medical device of claim 1, wherein the insulating material is coupled to a portion of at least one of the one or more conductive arms of the second electrode.

8. The medical device of claim 1, wherein the insulating material is coupled to a portion of the first and second electrodes.

9. The medical device of claim 1, further comprising an energy source coupled with the first electrode and the second electrode.

10. The medical device of claim 9, wherein the energy source includes a radio frequency generator.

11. The medical device of claim 9, wherein the energy source and the first electrode and second electrode are cooperatively configured to operate the first electrode and the second electrode in a unipolar mode.

12. The medical device of claim 9, wherein the energy source and the first electrode and second electrode are cooperatively configured to operate the first electrode and the second electrode in a bipolar mode.

13. The medical device of claim 1, wherein the first electrode and the second electrode are substantially coaxial.

* * * * *